(12) United States Patent
Hodge

(10) Patent No.: US 11,880,493 B2
(45) Date of Patent: Jan. 23, 2024

(54) WEARABLE DEVICES IN A CONTROLLED ENVIRONMENT

(71) Applicant: **GLOBAL TEL*LINK CORPORATION**, Reston, VA (US)

(72) Inventor: Stephen L. Hodge, Aubry, TX (US)

(73) Assignee: **Global Tel*Link Corporation**, Reston, VA (US)

( * ) Notice: Subject to any disclaimer, the term of this patent is extended or adjusted under 35 U.S.C. 154(b) by 1028 days.

(21) Appl. No.: 15/469,992

(22) Filed: Mar. 27, 2017

(65) Prior Publication Data
US 2018/0275859 A1   Sep. 27, 2018

(51) Int. Cl.
*G06F 21/00* (2013.01)
*G06F 21/62* (2013.01)
(Continued)

(52) U.S. Cl.
CPC ............ *G06F 21/629* (2013.01); *A61B 5/117* (2013.01); *A61B 5/1171* (2016.02); *A61B 5/681* (2013.01); *G06F 1/163* (2013.01); *G06F 1/1624* (2013.01); *G06F 1/1662* (2013.01); *G06F 1/1673* (2013.01); *G06F 3/0426* (2013.01);
(Continued)

(58) Field of Classification Search
CPC ..... A61B 5/117; A61B 5/681; A61B 5/14542; A61B 5/1171; A61B 5/024; A61B 5/01; G06F 1/163; G06F 2221/2111; G06F 3/04847; G06F 3/0481; G06F 3/0484; G06F 21/629; G06F 1/1673; G06F 21/34; G06F 1/1662; G06F 3/0426; G06F 1/1624; G06F 3/04886; G06F 3/0485; G06F 3/04883; G06F 3/0482; H04L 63/102; H04L 67/12; H04W 12/08
See application file for complete search history.

(56) References Cited

U.S. PATENT DOCUMENTS 4,495,386 A   1/1985  Brown et al.
5,255,306 A  10/1993  Melton et al.
(Continued)

FOREIGN PATENT DOCUMENTS

WO   WO-2016125063 A1 *  8/2016  ............. G04G 17/02

OTHER PUBLICATIONS

"Criminal Calls: A Review of the Bureau of Prisons' Management of Inmate Telephone Privileges," U.S. Department of Justice, Office of the Inspector General, Aug. 1999, 166 pages.
(Continued)

*Primary Examiner* — Cesar B Paula
*Assistant Examiner* — David Faber
(74) *Attorney, Agent, or Firm* — Sterne, Kessler, Goldstein & Fox P.L.L.C.

(57) ABSTRACT

A wearable device and method for operating the wearable device in a wearable device communication system in a controlled environment is disclosed. The wearable device includes at least one module configured to customize an inmate interface on the wearable device based at least in part of an inmate profile and an administrative rule. In some embodiments, the inmate interface is a keyboard. The wearable device also includes additional modules that enable the wearable device to monitor information regarding at least one of the inmate of the wearable device and the physical environment in which the wearable device is located.

20 Claims, 19 Drawing Sheets

(51) Int. Cl.
*G06F 3/04886* (2022.01)
*G06F 1/16* (2006.01)
*A61B 5/1171* (2016.01)
*H04L 9/40* (2022.01)
*A61B 5/117* (2016.01)
*A61B 5/00* (2006.01)
*G06F 3/0482* (2013.01)
*H04W 12/08* (2021.01)
*G06F 21/34* (2013.01)
*G06F 3/042* (2006.01)
*G06F 3/04847* (2022.01)
*G06F 3/0481* (2022.01)
*G06F 3/0484* (2022.01)
*A61B 5/024* (2006.01)
*A61B 5/01* (2006.01)
*H04L 67/12* (2022.01)
*A61B 5/145* (2006.01)

(52) U.S. Cl.
CPC .......... *G06F 3/0481* (2013.01); *G06F 3/0482* (2013.01); *G06F 3/0484* (2013.01); *G06F 3/04847* (2013.01); *G06F 3/04886* (2013.01); *G06F 21/34* (2013.01); *H04L 63/102* (2013.01); *H04W 12/08* (2013.01); *A61B 5/01* (2013.01); *A61B 5/024* (2013.01); *A61B 5/14542* (2013.01); *G06F 2221/2111* (2013.01); *H04L 67/12* (2013.01)

(56) References Cited

U.S. PATENT DOCUMENTS

| | | |
|---|---|---|
| 5,896,556 A | 4/1999 | Moreland et al. |
| 6,054,928 A * | 4/2000 | Lemelson .......... G08B 21/0423 455/100 |
| 6,058,173 A | 5/2000 | Penfield et al. |
| 6,668,045 B1 | 12/2003 | Mow |
| 6,965,590 B1 | 11/2005 | Schmidl et al. |
| 7,085,359 B2 | 8/2006 | Crites et al. |
| 7,106,843 B1 | 9/2006 | Gainsboro et al. |
| 7,218,993 B2 | 5/2007 | Yasukawa et al. |
| 7,254,708 B2 | 8/2007 | Silvester |
| 7,280,816 B2 | 10/2007 | Fratti et al. |
| 7,333,798 B2 | 2/2008 | Hodge |
| 7,363,330 B1 * | 4/2008 | Ellman ................. G06F 16/182 707/634 |
| 7,366,782 B2 | 4/2008 | Chong et al. |
| 7,529,357 B1 | 5/2009 | Rae et al. |
| 7,587,067 B1 | 9/2009 | Schiller |
| 7,742,581 B2 | 6/2010 | Hodge et al. |
| 7,804,941 B2 | 9/2010 | Keiser et al. |
| 7,860,222 B1 | 12/2010 | Sidler et al. |
| 7,899,167 B1 | 3/2011 | Rae |
| 8,019,354 B2 | 9/2011 | Rae et al. |
| 8,031,052 B2 | 10/2011 | Polozola |
| 8,370,206 B2 | 2/2013 | Collins |
| 8,428,559 B2 | 4/2013 | Silva |
| 8,498,937 B1 | 7/2013 | Shipman, Jr. et al. |
| 8,571,525 B2 | 10/2013 | Weinstein et al. |
| 8,584,019 B1 * | 11/2013 | Gala .................. G06Q 50/00 715/810 |
| 8,639,926 B2 | 1/2014 | Brown et al. |
| 8,646,056 B2 | 2/2014 | Poplett |
| 8,832,374 B1 * | 9/2014 | Schaefers ............. G06F 21/32 711/115 |
| 8,917,848 B2 | 12/2014 | Torgersrud et al. |
| 9,094,500 B1 | 7/2015 | Edwards |
| 9,124,763 B2 | 9/2015 | Humphries |
| 9,129,230 B2 * | 9/2015 | Lewis ................... G06Q 10/00 |
| 9,143,886 B1 * | 9/2015 | Abou-El-Ella ......... H04W 4/50 |
| 9,232,051 B2 | 1/2016 | Torgersrud et al. |
| 9,262,604 B2 | 2/2016 | Kimbrell |
| 9,282,188 B2 | 3/2016 | Hodge et al. |
| 9,307,386 B2 | 4/2016 | Hodge et al. |
| 9,491,176 B1 | 11/2016 | Jaini et al. |
| 9,614,954 B2 | 4/2017 | Hodge et al. |
| 9,614,955 B2 | 4/2017 | Hodge et al. |
| 9,622,079 B2 * | 4/2017 | Giordano ............ H04W 12/082 |
| 9,661,128 B2 | 5/2017 | Hodge et al. |
| 9,674,338 B2 | 6/2017 | Hodge et al. |
| 9,843,589 B2 * | 12/2017 | Gupta .................... H04L 67/01 |
| 9,866,680 B2 | 1/2018 | Hodge et al. |
| 9,871,915 B2 | 1/2018 | Hodge et al. |
| 9,888,108 B2 | 2/2018 | Hodge et al. |
| 9,892,242 B1 | 2/2018 | Hodge |
| 9,973,828 B1 * | 5/2018 | Jaini .................. H04N 21/2541 |
| 10,104,198 B1 * | 10/2018 | Ho .......................... H04L 67/60 |
| 2002/0071537 A1 | 6/2002 | Gainsboro |
| 2002/0125886 A1 * | 9/2002 | Bates .................... H04L 63/104 324/309 |
| 2003/0036381 A1 | 2/2003 | Nagashima |
| 2003/0086546 A1 | 5/2003 | Falcone et al. |
| 2003/0126470 A1 | 7/2003 | Crites et al. |
| 2003/0198325 A1 | 10/2003 | Bayne |
| 2003/0224764 A1 | 12/2003 | Baker |
| 2004/0210773 A1 * | 10/2004 | Markosi, III ........... G06F 21/55 709/224 |
| 2005/0265529 A1 | 12/2005 | Hogg, Jr. et al. |
| 2006/0062355 A1 | 3/2006 | Leonard |
| 2006/0176169 A1 | 8/2006 | Doolin et al. |
| 2007/0041545 A1 | 2/2007 | Gainsboro |
| 2007/0047694 A1 | 3/2007 | Bouchard et al. |
| 2007/0057763 A1 | 3/2007 | Blattner et al. |
| 2008/0057976 A1 | 3/2008 | Rae et al. |
| 2008/0200156 A1 | 8/2008 | Hicks et al. |
| 2009/0080629 A1 | 3/2009 | Rokosky et al. |
| 2009/0265106 A1 * | 10/2009 | Bearman ................ G06Q 10/00 701/300 |
| 2010/0062833 A1 | 3/2010 | Mattice et al. |
| 2010/0153951 A1 * | 6/2010 | Jones .................. G06F 11/3089 718/100 |
| 2010/0189228 A1 | 7/2010 | Seyfetdinov |
| 2010/0222179 A1 * | 9/2010 | Temple ............... A63B 71/0622 482/8 |
| 2010/0260173 A1 | 10/2010 | Johnson |
| 2011/0158223 A1 | 6/2011 | Liu et al. |
| 2011/0213618 A1 | 9/2011 | Hodge et al. |
| 2011/0237226 A1 | 9/2011 | Dhuna |
| 2012/0099714 A1 | 4/2012 | Hodge |
| 2012/0252411 A1 | 10/2012 | Johsgard et al. |
| 2012/0262271 A1 | 10/2012 | Torgersrud et al. |
| 2013/0012234 A1 * | 1/2013 | Tufty .................... H04W 4/029 455/456.6 |
| 2013/0179210 A1 | 7/2013 | Collins |
| 2013/0263227 A1 | 10/2013 | Gongaware et al. |
| 2013/0293378 A1 | 11/2013 | Aninye et al. |
| 2013/0311364 A1 | 11/2013 | Shipman et al. |
| 2014/0032691 A1 | 1/2014 | Barton et al. |
| 2014/0044242 A1 | 2/2014 | Hodge et al. |
| 2014/0089849 A1 | 3/2014 | Choi et al. |
| 2014/0108649 A1 | 4/2014 | Barton |
| 2014/0109174 A1 | 4/2014 | Barton et al. |
| 2014/0115466 A1 | 4/2014 | Barak et al. |
| 2014/0149506 A1 * | 5/2014 | Yuan ....................... H04L 67/01 709/204 |
| 2014/0219432 A1 | 8/2014 | Bengston et al. |
| 2014/0266703 A1 * | 9/2014 | Dalley, Jr. ............. G08B 25/00 340/10.51 |
| 2014/0267547 A1 | 9/2014 | Torgersrud et al. |
| 2014/0273929 A1 | 9/2014 | Torgersrud |
| 2014/0280559 A1 * | 9/2014 | Torgersrud ............ H04L 67/535 709/204 |
| 2014/0282868 A1 | 9/2014 | Sheller et al. |
| 2014/0287715 A1 | 9/2014 | Hodge et al. |
| 2014/0379843 A1 | 12/2014 | Schaefers |
| 2015/0077245 A1 * | 3/2015 | Kaufman ........... A61B 5/14551 340/539.12 |
| 2015/0097961 A1 * | 4/2015 | Ure ....................... H04W 12/06 348/159 |
| 2015/0215254 A1 * | 7/2015 | Bennett ............... H04M 3/2281 709/206 |

(56) References Cited

U.S. PATENT DOCUMENTS

| | | | |
|---|---|---|---|
| 2015/0237052 | A1 | 8/2015 | Brique et al. |
| 2015/0242629 | A1 | 8/2015 | Lindo et al. |
| 2016/0034046 | A1* | 2/2016 | Waddell ............... G06F 3/0237 345/173 |
| 2016/0055323 | A1 | 2/2016 | Stuntebeck et al. |
| 2016/0066182 | A1 | 3/2016 | Hodge et al. |
| 2016/0088021 | A1 | 3/2016 | Jayanti Venkata et al. |
| 2016/0127378 | A1 | 5/2016 | Gupta |
| 2016/0219146 | A1 | 7/2016 | Hodge et al. |
| 2016/0267257 | A1 | 9/2016 | Wisgo |
| 2016/0330084 | A1 | 11/2016 | Hunter et al. |
| 2016/0346607 | A1* | 12/2016 | Rapfogel ............ G09B 19/0038 |
| 2016/0381212 | A1 | 12/2016 | Hodge et al. |
| 2016/0381219 | A1 | 12/2016 | Hodge et al. |
| 2016/0381556 | A1 | 12/2016 | Hodge et al. |
| 2017/0061006 | A1 | 3/2017 | Hildebrand et al. |
| 2017/0084150 | A1 | 3/2017 | Keyton |
| 2017/0177892 | A1 | 6/2017 | Tingstrom et al. |
| 2017/0193622 | A1 | 7/2017 | Rosado |
| 2017/0208468 | A1 | 7/2017 | Hodge et al. |
| 2017/0222977 | A1* | 8/2017 | Newell ................... H04W 4/50 |
| 2018/0014778 | A1* | 1/2018 | Cronin ................. G04G 21/025 |

OTHER PUBLICATIONS

European Search Report and Opinion directed to European Patent Application No. 14769931.8, dated Oct. 26, 2016; 10 pages.

International Search Report and Written Opinion of the International Searching Authority, directed to related International Patent Application No. PCT/US14/31339, dated Nov. 6, 2014; 19 pages.

Knox, "The Problem of Gangs and Security Threat Groups (STG's) in American Prisons Today: Recent Research Findings From the 2004 Prison Gang Survey," National Gang Crime Research Center, 2005; 67 pages.

Rey, R.F., ed., "Engineering and Operations in the Bell System," 2nd Edition, AT&T Bell Laboratories: Murray Hill, NJ, 1983, 884 pages.

Rosenberg, et al., "SIP: Session Initial Protocol," Network Working Group, Standard Track, Jun. 2002; 269 pages.

U.S. Appl. No. 61/801,861, "Handheld Video Visitation," to Torgersrud, et al., filed Mar. 15, 2013.

Winterdyk et al., "Managing Prison Gangs," Journal of Criminal Justice, vol. 38, 2010; pp. 730-736.

International Search Report and Written Opinion of the International Searching Authority directed to related International Patent Application No. PCT/US2018/024611, dated Jun. 11, 2018; 7 pages.

\* cited by examiner

WEARABLE DEVICES IN A CONTROLLED ENVIRONMENT

BACKGROUND

Field

This disclosure relates to wearable devices having a dynamic interface and a method for their use within a controlled environment.

Background

In a controlled environment, such as a correctional facility or prison, administrators may provide opportunities for entertainment and communication to inmates through restricted access to mobile devices such as tablets and/or smart phones. By their nature, such mobile devices are portable.

BRIEF DESCRIPTION OF THE DRAWINGS/FIGURES

However, because of their portability, tablets and smart phones present issues as they may be stolen, lost, dropped, and/or otherwise easily broken. Additionally, while such devices may have certain security mechanisms to link a mobile device to a specific inmate, such security mechanisms do not necessarily stop other inmates from stealing or harming the inmate to use their mobile device.

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 1:
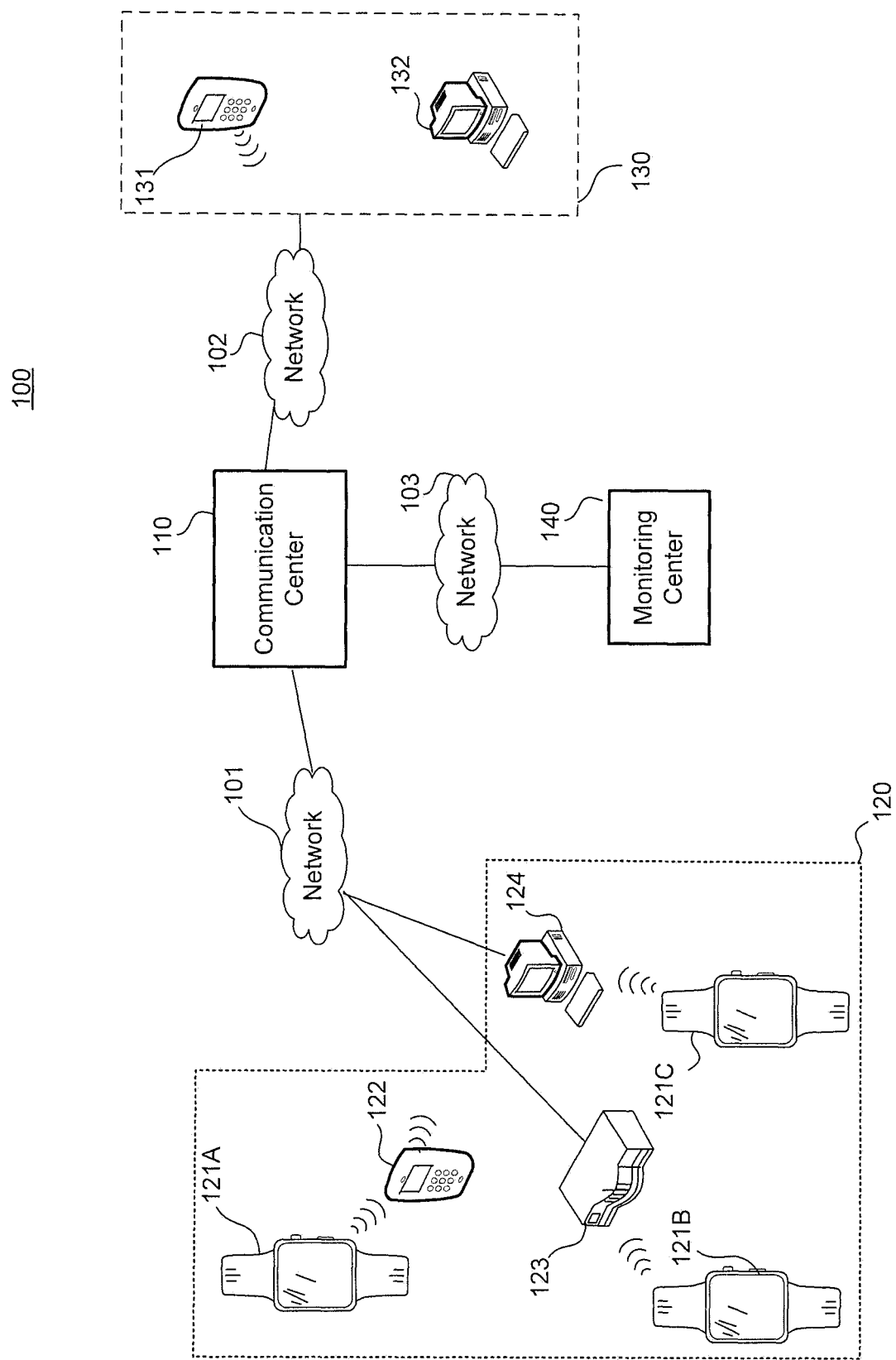
FIG. 1 illustrates a block diagram of an exemplary wearable device communication system, according to embodiments of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" shall be understood to include at least one of software, firmware, and hardware (such as one or more circuit, microchip, or device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner.

The following Detailed Description of the exemplary embodiments will so fully reveal the general nature of the disclosure that others can, by applying knowledge of those skilled in relevant art(s), readily modify and/or customize for various applications such exemplary embodiments, without undue experimentation, without departing from the spirit and scope of the disclosure. Therefore, such modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

Exemplary Wearable Device Communication System

FIG. 1 illustrates a block diagram of an exemplary wearable device communication system 100, according to embodiments of the present disclosure. In some embodiments, wearable device communication system 100 includes communication center 110 which is configured to transmit information between inmate communication system 120, outsider communication system 130, and/or monitoring center 140. An inmate of wearable device communication system utilizes inmate communication system 120 in a number of ways including receiving wearable device information from communication center 110, transmitting wearable device information to communication center 110, and communicating with an outside party utilizing outsider communication system 130.

In some embodiments, wearable device information includes voice calls, video calls, text messages, email messages, multimedia content (e.g., video, music, educational programs, games), interface information (e.g., inputs received on an input interface at inmate communication system 120, outputs to be displayed on inmate communication system 120), control information, browser information, and/or application information from applications stored on inmate communication system 120.

In some embodiments, inmate communication system 120 includes one or more devices provided to inmates within a controlled environment, such as a correctional facility, and where the one or more devices include wearable devices 121A-121C. Inmate communication system 120 can further include devices such as a companion wireless communication device 122, wireless access point 123 (e.g., gateway or router), and/or kiosk 124. In some embodiments, wearable devices 121A-121C are watches having a touchscreen interface.

The phrase "wearable devices" also refers to devices that can be inserted within an inmate's body. Such devices can be configured to provide locator and inmate identification functionality. Such devices can be powered by a blood battery electrolyte system.

In some embodiments, wearable devices 121A-121C have wireless communication capabilities. In an embodiment, wearable device 121A communicates with network 101 through a connection with wireless communication device 122. The communication with wireless communication device 122 may be a wireless connection, such as Bluetooth™ or Wi-Fi connections, or through a wired connection such as with a USB cable. In an embodiment, wearable device 121B communicates with network 101 through a connection with wireless access point 123. The communication with wireless access point 123 may be a wireless connection, such as Bluetooth™ or Wi-Fi connections. In an embodiment, wearable device 121C communicates with network 101 through a connection with kiosk 124. The communication with kiosk 124 may be a wireless connection, such as Bluetooth™ or Wi-Fi connections. Wireless communication device 122 can be implemented as any mobile device such as, but not limited to, a smartphone, a tablet, or a laptop device.

Inmate communication system 120 connects to communication center 110 via network 101, which may include any or all of a Local-Area Network (LAN), a Wide-Area Network (WAN), or the Internet, depending on the location of communication center 110 in relation to inmate communication system 120. For example, network 101 is implemented as a LAN when communication center 110 and inmate communication system 120 are both located at a controlled environment. In another example, network 101 is implemented as a WAN or the Internet when communication center 110 is located at a different location than inmate communication system 120.

Outsider communication system 130 is communicatively coupled to communication center 110 and includes one or more devices available to outsiders to the controlled environment and includes any and all communications devices such as a wireless communication device 131 and/or computer station 132. In an embodiment, outside communication system 130 may be located within the controlled environment, such as in a designated area or room of the controlled environment. In another embodiment, outside communication system 130 may be located outside of the controlled environment such as in the outsider's home. Outsider communication system 130 connects to communication center 110 via network 103, which may include any or all of a WAN, the Internet, and/or a Public Switched Telephone Network (PSTN). The WAN may facilitate communications with other nearby prisons, such as those within the same county, state, etc.

In an embodiment, wearable device communication system 100 also includes monitoring center 140 for monitoring wearable devices 121A-121C within wearable device communication system 100. Monitoring of wearable devices 121A-121C includes but is not limited to monitoring user inputs, the user interface being displayed, and communications to and from wearable devices 121A-121C. Moreover, monitoring by monitoring center 140 can occur both automatically and manually (e.g., initiated a reviewer). Monitoring center 140 receives communications and data from communication center 110 via network 105, which may include any or all of a LAN, a WAN, or the Internet. Monitoring center 140 receives wearable device information related to interactions and communications involving all devices including wearable devices 121A-121C in wearable device communication system 100 through communication center 110. Monitoring center 140 may store and/or analyze the received interactions and communications. Monitoring center 140 may further provide instructions to devices in wearable device communication system 100 based on the analysis performed on the received interactions and communications.

In some embodiments, the wearable device information includes but is not limited to an audio stream, a video stream, actions performed by the users on their wearable device, content viewed by users through their wearable device, data, such as biometric data, regarding the wearer of each wearable device, and/or content requested by users through their wearable device. Based on this wearable device information, monitoring center may provide instructions to affect certain functionality of the wearable devices. Such instructions include but are not limited to modifying a dynamic user interface of the wearable device, modifying the content that may be viewed or utilized by the inmate, and/or transmitting communications to be output to the inmate through the wearable devices.

In some embodiments, a dynamic user interface is a graphical user interface that is adapted based on any number of conditions including but not limited to a user's typing history, applications, location of the wearable device, and administrative rules provided by authorized personnel of the controlled environment. Modifying the dynamic user interface includes providing different input interfaces through which the inmate may provide input for applications on the wearable device. For example, wearable devices with touchscreen displays such as wearable devices 121A-121C may have different keyboards and/or interfaces based on different applications or locations within the controlled environment. Modifying the dynamic user interface of the wearable device may include selecting a different keyboard for use by the user based, but are not limited to, different applications, preferences of the user, and/or location of the wearable device within the controlled environment.

In some embodiments, modifying the dynamic user interface includes adjusting the content that can be accessed on a wearable device. For example, monitoring center 140 may send a control signal to any of wearable devices 121A-121C based on a context of the wearable devices 121A-121C. The control signal may cause wearable devices 121A-121C to display only certain applications and to display certain applications as not being accessible. Contexts can include but are not limited to different applications, preferences of the user, and/or location of the wearable device within the controlled environment.

The authorized content is any content authorized to be provided to and/or utilized by one of wearable devices 121A-121C. For example, authorized content includes a list of accessible websites, games, multimedia content, applications such as a word processing application, a text messaging application, a video conference application, and a multimedia application.

In an embodiment, content is authorized on an individual basis (i.e., applies only to a specific user or users and/or specific wearable devices based on, for example, the profile information) or on a global basis (i.e., applies to all wearable devices in wearable device communication system 100 through communication center 110). Monitoring center 140 can modify user profiles to include information that indicates the content for which users and/or wearable devices are authorized and not authorized. For global restrictions, monitoring center 140 can send information that indicates the content that is authorized and not authorized for all users of wearable device communication system 100.

Exemplary Communication Center

Figure 2:
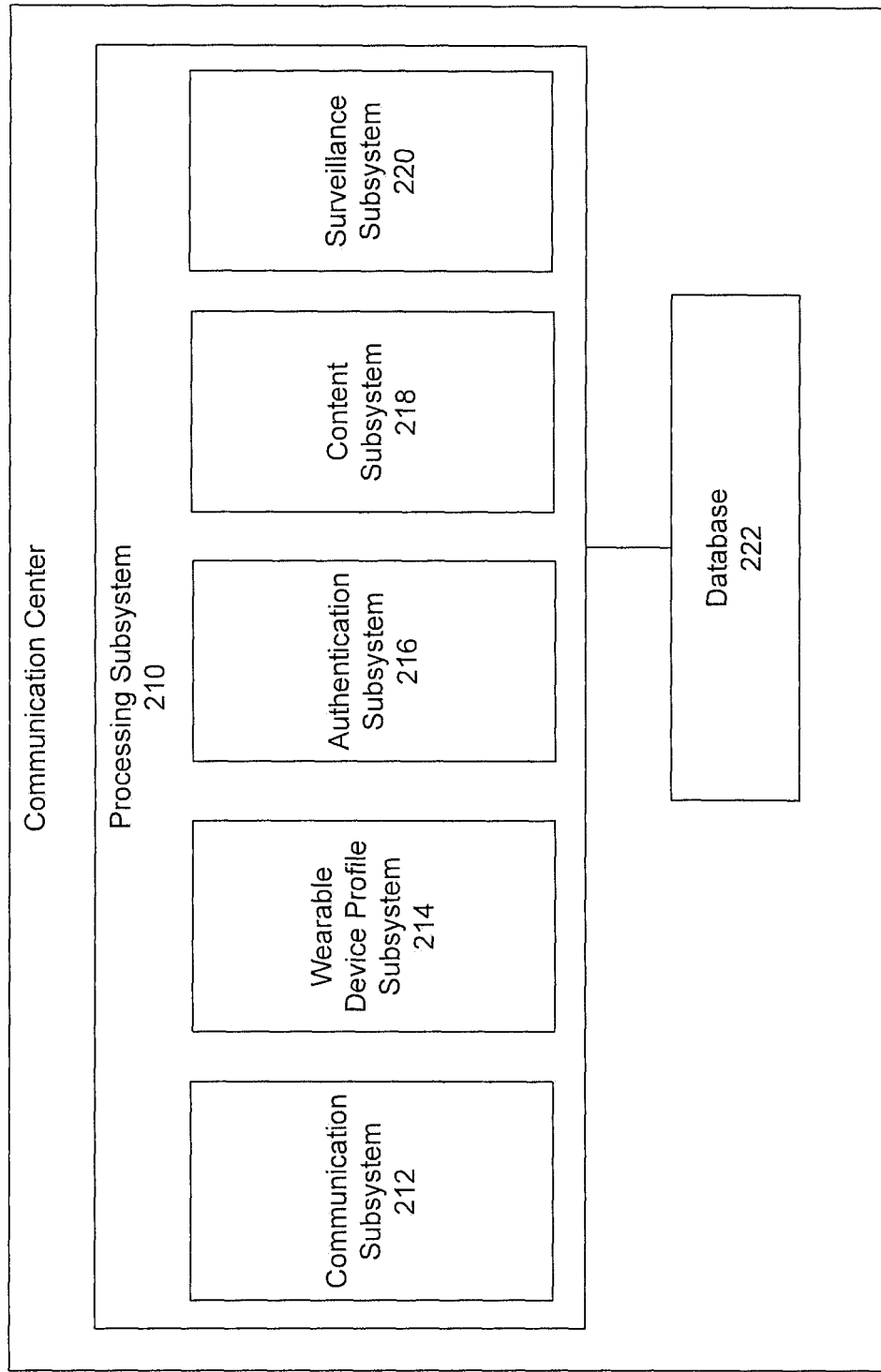
FIG. 2 illustrates a block diagram of an exemplary communication center for use in the exemplary wearable device communication system of FIG. 1, according to embodiments of the present disclosure.

FIG. 2 illustrates a block diagram of communication center 200, according to embodiments of the present disclosure. In an embodiment, communication center 200 represents an exemplary embodiment of communication center 110 of FIG. 1. Communication center 200 includes but is not limited to processing subsystem 210 and database 222. Processing subsystem 210 includes one or more processors, computers, or servers identified as subsystems and can be constructed as individual physical hardware devices, or as virtual devices, such as a virtual server. The number of processing subsystems can be scaled to match the number of simultaneous user connections desired to be supported by an wearable device communication system such as wearable device communication system 100 of FIG. 1. Processing subsystem 210 includes but is not limited to communication subsystem 212, profile subsystem, 214, authentication subsystem 216, content subsystem 218, and surveillance subsystem 220.

In an embodiment, communication subsystem 212 controls the routing of communications to an end destination such as one or more wearable devices within inmate communication system 120, one or more devices within outsider communication system 130, or monitoring center 140. Communication subsystem 212 performs switching required to electrically connect the one or more devices within inmate communication system 120 and one or more devices within outsider communication system 130. Further, communication subsystem 212 logs communication information, including time of communications and parties involved in the communications, and stores the logs and communications as files. The files stored by communication subsystem 212 can be stored indefinitely for use by monitoring center 140 in monitoring and investigation of an inmate and/or communication. Communication subsystem 212 also determines whether a communication should be monitored such that privileged communications such as attorney/client, doctor/client, or investigative communications are not monitored. Criteria for monitoring a communication may be based on jurisdictional requirements and/or identities of the parties.

In an embodiment, communication subsystem 212 is configured to receive contact information such as a phone number, email address, internet protocol address or other identifying data of the users of a wearable device. The received contact information may be used by each of the subsystems of the communication center 200 for identifying respective data and processes related to the contact information, such as purported identities of parties involved in the communication.

Because there may be a variety of different communication standards employed by wearable devices, in some embodiments, communication subsystem 212 is also configured to perform format conversion of non-real time communications. Conversion of incoming and outgoing communications are performed, as needed, to be compatible with inmate communication device 120, outsider communication device 130, or monitoring center 140. The format conversion includes conversion of incoming communications and outgoing communications to be compatible with inmate communication system 120 or the monitoring center 130. Further, because communication subsystem 212 receives and transmits communications by way of a network, in an exemplary embodiment, communication subsystem 212 is configured to decrypt received communications and encrypt transmitting communications, for security purposes.

Wearable device profile subsystem 214 obtains and stores profile information on parties registered to use wearable devices and communicate via wearable device communication system 100. In an embodiment, profile subsystem 214 stores inmate profiles and outsider profiles. Profile subsystem 214 obtains information related to the parties from one or more of (a) a jail management system (JMS) or an offender management system (OMS) operated by the jurisdiction of the correctional facility, (b) public database containing information on the parties, or (c) a questionnaire provided by a web page, a personal approved number (PAN) list, or booking information. Information obtained by wearable device profile subsystem 214 may include personal information such as previous residences or correctional facilities, authorized contacts, family members, languages, special needs, medication requirements, etc.

In some embodiments, wearable device profile subsystem 214 also performs a registration process for those parties not enrolled or registered to use wearable device communication system 100. During the registration process, or at a later time, wearable device profile subsystem 214 determines accommodations and settings associated with a party and/or a party is able to select preferred settings for a communication. These accommodations and settings include, but are not limited to, preferences of each user of wearable device communication system 100, such as favorite websites, purchased content, and/or preferences for applications. Profile information can also include a user's medical history which could be utilized in medical applications, applications authorized to be used by the user, applications restricted from use by the user, and a user's typing history such as most frequently used words and most frequently used letters.

In an embodiment, wearable device profile subsystem 214 also receives authorization information indicating content that is authorized and not authorized for each profile. The information may be received from a monitoring system such as monitoring center 140 as illustrated in FIG. 1. Profile subsystem 214 can store the authorization information internally or in database 222. If the information is specific to a user or user(s), wearable device profile system 214 can also store the information as part of the user or user(s) profile(s). The authorization information is used to customize the interfaces of wearable device 300 by limiting or allowing access to the content by users of wearable device 300.

In an embodiment, wearable device profile subsystem 214 also includes administrator preferences provided by an administrator of wearable device communication system 100, such as a designated employee of the controlled environment. Administrator rules allow and restrict actions that can be performed within wearable device communication system 100. Administrator rules have higher priority than the preferences specified in the user profiles. In an embodiment, administrator preferences include global preferences that influence all users of wearable devices and inmate-specific preferences that only apply to specific inmates.

Administrator rules generally limit or allow actions that can be performed by users when using wearable devices. For example, the administrator can restrict all inmates and outsiders from accessing websites deemed to be inappropriate or certain applications and/or specify specific websites or applications that may be accessed while using wearable devices. Administrator rules can also specify allowable applications in specific areas in the controlled environment and restricted applications in specific areas in the controlled environment. As discussed above, an administrator can implement such restrictions on a global (all inmates of wearable devices) or inmate-specific basis.

In an embodiment, profiles in wearable device profile subsystem 214 controls content that is available to users for use on their wearable devices based on authorization information indicating authorized content and unauthorized content and administrator rules. The authorization information can be specific to a user or user(s) and/or applied globally to all users of wearable devices. Authorization information can indicate that a user or user(s) are not allowed to access certain content, such as websites, games, and/or applications, while using a wearable device. For example, if a user's profile indicates that the user is not allowed to access certain applications in a certain location of the controlled environment, the user would be prevented from being presented that information when the user and the wearable device are determined to be within the certain location.

In an embodiment, authentication subsystem 216 collects and stores identity data of inmates and outsiders authorized to access wearable device communication system 100. Identity data includes but is not limited to at least one of a username and password data, challenge questions, challenge answers, biometric data, device data such as make and model of a communication device, and/or location data. Biometric data includes one or more of a finger print, a hand print, a voice sample, an iris or retinal sample, an image of the user (2D or 3D), a hand geometry, a signature identification, an infrared camera identification, or any other biometric as deemed appropriate. The challenge question form of identity data may be a series of challenge questions, or a single challenge question such as the last four digits of an inmate's social security number, mother's maiden name, and the like. Authentication subsystem 216 is further configured to facilitate a secure communication between parties receiving/transmitting a communication by performing identity verifications to authenticate identities of purported parties. The identity verification includes logon verifications, such as username and password verifications, biometric verification, response to challenge questions, device verification, and/or location verification.

In an embodiment, authentication subsystem 216 tracks a user's biometric information from wearable devices. Authentication subsystem 216 can utilize the tracked biometric information to authenticate the user of the wearable devices. For example, when an inmate is issued a wearable device, the inmate's biometric information may be associated with the specific wearable device. Biometric information can include but is not limited to heart rate information, oxygen levels, fingerprint information, and/or voice information. In this manner, the monitoring center may passively authenticate users of wearable devices to ensure that the users are allowed to use their wearable devices. Authentication subsystem 216 can also, with the permission of the wearer of the wearable device, transmit biometric information to a doctor for participation in a remote telemedicine program where the doctor can attempt to diagnose or otherwise assist the wearer with medical advice.

In addition to biometric information, authentication subsystem 216 can also perform identity verification by receiving identity information such as one or more of a username and password, a response to a challenge question(s), a keypad or touch pad entry, a voice sample, a fingerprint sample, a retinal sample, a facial image (2D or 3D), device information such as a make and model of the communication device, and/or a location of the communication device, from a communication device (such as a device of inmate communication system 120 or outsider communication system 130) and comparing the identity information of the purported party with stored identity data that is associated with a wearable device. Authentication subsystem 216 also uses the collected information to register users of wearable device communication system 100.

In some embodiments, authentication subsystem 216 also stores administrative rules that control how content can be displayed on wearable devices in wearable device communication system 100. As noted above, administrative rules allow authorized personnel to control actions performed and communications transmitted within wearable device communication system 100. Administrative rules can be provided by and stored in monitoring center 140. Administrative rules allow for authorized personnel associated with the controlled environment to remotely control functionality of the wearable device including the dynamic user interface and operations of components of the wearable device. Administrative rules specify authorized functions that may be performed by a wearable device including the specific operations of components of the wearable device. Examples of authorized functions include, but are not limited to, displaying dynamic user interfaces, displaying available applications, video recording (e.g., for video calls), audio recording, access to applications, and/or activating a surveillance mode such as biometric surveillance or environmental surveillance.

In some embodiments, an administrative rule can also specify which components of the wearable device are allowed to function. For example, authorized personnel can push or otherwise transmit a rule to deactivate the video module of a user who is using the camera of the wearable device for inappropriate purposes. In some embodiments, functionality of wearable devices can be configured to operate with corresponding administrative rules. For example, a controlled environment may establish an administrative rule that prevents all wearable devices from allowing inmates to access any applications while inmates are walking between areas in the controlled environment. Administrative rules can also contain identifiers that allow wearable devices to verify that the administrative rules are from authorized personnel of the controlled environment and prevent unauthorized rules from modifying the interfaces of the wearable devices.

Content subsystem 218 is responsible for retrieving and routing content to and from inmate communication system 120 such as wearable devices 121A-121C. Content subsystem 218 can be implemented as any number of servers, and is configured to facilitate the provision of content (e.g., games, applications, multimedia, emails, web) to inmate communication system 120. In some embodiments, content subsystem 218 retrieves content from a content source such as database 222, which is located in communication center 200. In other embodiments, database 222 may be located in monitoring center 140 or distributed between communication center 200 and monitoring center 140. All content that can be provided within wearable communication system 100 is pre-screened and authenticated by the controlled environment, such as through communication center 200. Content subsystem 218 is configured to receive requests identifying content to be provided to inmate communication system 120.

In some embodiments, surveillance subsystem 220 consists of any number of servers, and manages and facilitates communications between subsystems of communication center 200 and devices external to the communication center, such as any device within inmate communication system 120 and outsider communication system 130. Surveillance subsystem 220 is responsible for receiving surveillance information from wearable devices 121A-121C. Surveillance information can detected by certain modules of each wearable device and includes but is not limited to a user's biometric information and environmental conditions of the user's current environment. Environmental conditions include audio information detected by a microphone of a wearable device and video information detected by a camera of the wearable device. Surveillance subsystem 220 receives surveillance information from wearable devices and can provide the surveillance information to a monitoring center for storage and analysis.

In some embodiments, surveillance subsystem 220 also enables surveillance capability by allowing for monitoring center 140 to remotely activate wearable devices 121A-121C. Surveillance capability includes but is not limited to performing surveillance of users of wearable devices and performing surveillance of current conditions of the controlled environment in which the wearable devices are distributed. For example, surveillance of users of wearable devices includes monitoring a user's biometric information (e.g., heart rate, oxygen levels, and/or temperature) such as through a biometric module in the wearable device and/or monitoring a user's interactions with his wearable device.

Surveillance of the controlled environment includes activating a microphone and/or camera of the wearable device to record current conditions of the controlled environment. Monitoring center 140 may receive the recorded information for analysis. In this manner, monitoring center 140 can utilize wearable devices to monitor and view the current physical surroundings of all users in wearable device communication system 100. Any and all information from any of wearable devices could be routed to monitoring center 140 through communication center 200.

In an embodiment, surveillance subsystem 220 can correlate surveillance information with stored profiles of the user(s). Surveillance subsystem 220 can store the surveillance information in database 222 and associate the surveillance information, such as a user's biometric information or a user's recorded conversation, with the user's profile in database 222 and/or wearable device profile subsystem 214. The user's profile, when storing the user's biometric information, may include the user's medical history which can be utilized when the user starts a medical application, such as a telemedicine application, on a wearable device to allow a doctor, who may be located at a remote location, to examine the user's information to perform a limited diagnosis or assist the user with certain medical actions, such as injection of medicine using a needless jet syringe applicator associated with the medical application.

Database 222 consists of any number of databases and/or servers, and stores and organizes data in a relational database. Database 222 runs a database management system, such as MYSQL™, to provide an example. Database 222 includes approved content that can be provided to users of inmate communication system 120 while using a wearable device. Database 222 also includes organized data such that respective identity data, authentication data, jurisdictional requirements and rules, and settings that are indexed and linked to allow access to data for each of the parties involved in a communication and data associated with each of the parties.

Exemplary Wearable Device

Figure 3:
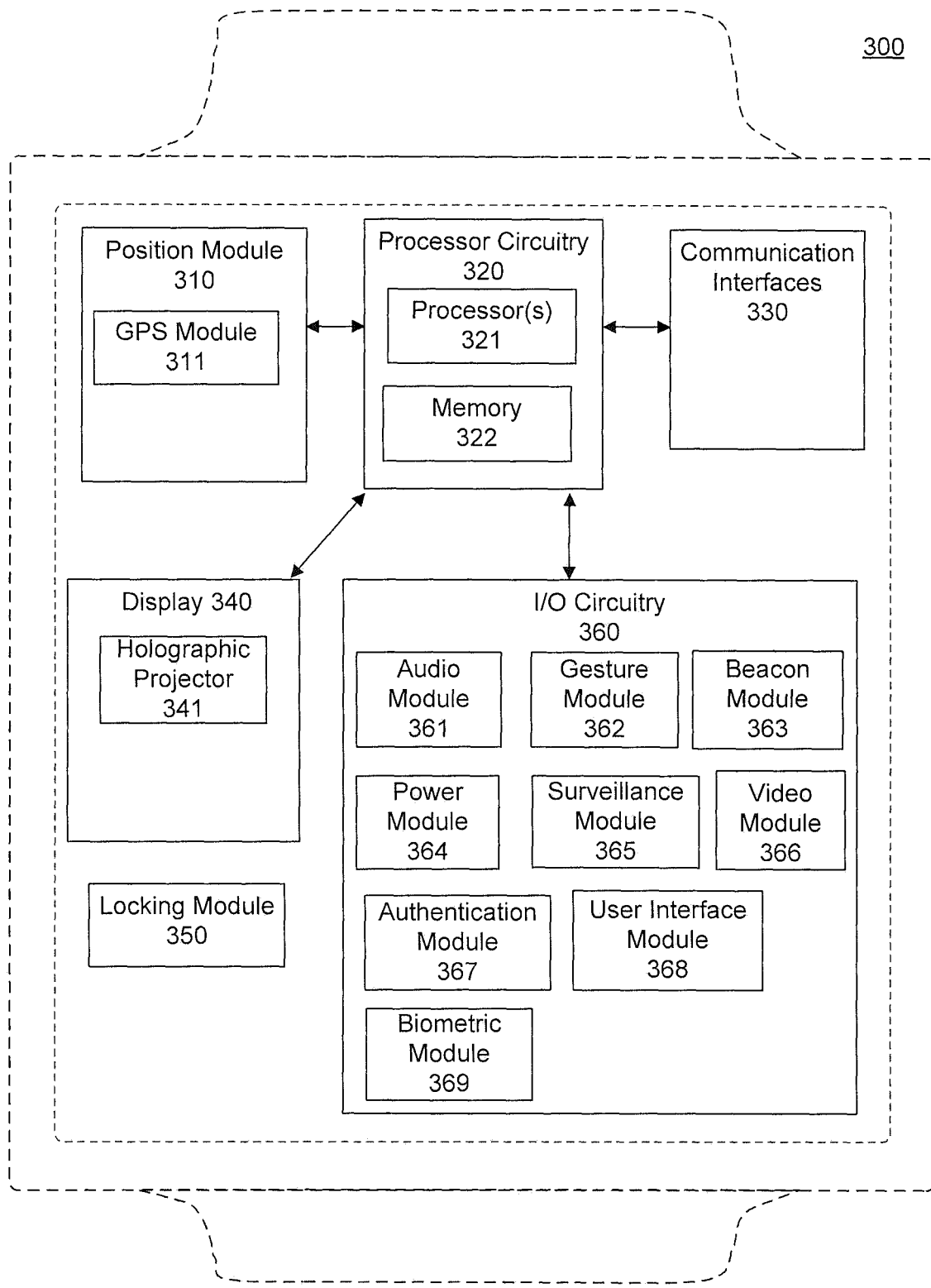
FIG. 3 illustrates a block diagram of an exemplary wearable device for use in the exemplary wearable device communication system of FIG. 1, according to embodiments of the present disclosure.

FIG. 3 illustrates a block diagram of wearable device 300, according to embodiments of the present disclosure. Wearable device 300 may be an exemplary embodiment of any of wearable devices 121A-121C as illustrated in FIG. 1. In an embodiment, wearable device 300 includes position module 310, processor circuitry 320, communication interfaces 330, display 340, locking module 350, and input/output circuitry 360, which all may be communicatively coupled to each other.

Position module 310 provides location functionality that allows wearable device 300 to receive and provide location-related information. In some embodiments, position module 310 includes GPS module 311. Position module can provide location information, such as GPS coordinates, to a monitoring center, such as monitoring center 140. The monitoring center may then utilize the GPS coordinates to determine the location and/or specific room within the controlled environment in which wearable device 300 is located. Position module 310 may also include indoor positioning systems (IPS) technology, accelerometers, and/or gyroscopes to determine position and motion of wearable device 300.

Processor circuitry 320 includes one or more processors 321, circuitry, and/or logic configured to control the overall operation of communication device 300, including the operation of position module 310, communication interfaces 330, display 340, locking module 350, and input/output modules 360. Processor circuitry 321 further includes memory 322 to store data and instructions. Memory 322 may be any well-known volatile and/or non-volatile memory that is removable and/or non-removable.

Communication interfaces 330 include one or more transceivers, transmitters, and/or receivers that communicate via a wireless interface, such as through one or more antennas 322, or a wired interface, such as through a USB cable. For example, communication interface 330 includes a component, such as a Bluetooth transceiver, that enables Bluetooth communication between wearable device 300 and an external device that also has Bluetooth capability, such as a smartphone, a tablet, a wireless headset, and/or wireless earbuds. In an embodiment, communication interfaces 330 are configured to transmit and receive communications between an inmate and an outsider via network 101 and network 103, as illustrated in FIG. 1. In an embodiment, communication interfaces 330 connect wearable device 300 with other devices such as a mobile device, a kiosk, an access point, a beacon, and/or external input devices such as a keyboard, mouse, camera, or touch interface.

Display 340 is a component for displaying content to a user. In some embodiments, display 340 is a touchscreen and receives touch inputs from a user of wearable device 300. In some embodiments, display 340 can also include a holographic projector 341 for projecting content onto an external surface such as a table or a user's forearm. In some embodiments, content displayed on display 340 and content projected by holographic projector 341 are different and can interact with each other. For example, content displayed on display 340 can be a text window that displays messages sent, messages received, and messages drafted while content projected by holographic projector 341 can be a keyboard that interacts with the text window on display 340.

Locking module 350 is a component that prevents users of wearable devices from removing the wearable devices. In some embodiments, wearable devices are permanently attached to users. Permanently attached means that the user of the wearable device cannot remove the wearable device under any condition. For example, the user is an inmate and the controlled environment is a prison. Only authorized personnel such as an administrator of the controlled environment may remove a permanently attached wearable device. In some embodiments, authorized personnel can remotely send a signal (e.g., over a network) to locking module 350 to unlock the wearable device. In some embodiments, authorized personnel use a physical device that transmits a signal when in certain proximity to the wearable device to locking module 350 to unlock the wearable device.

In some embodiments, wearable devices are semi-permanently attached to users. Semi-permanently attached means that the user of the wearable device can remove the wearable device but only under certain conditions. For example, locking module 350 may provide a timer functionality which keeps the wearable device locked for a specific period of time (e.g., for 10 hours) or a specific period of the day (e.g., between 7:00 AM and 10:00 PM).

In some embodiments, wearable devices do not include locking module 350. In such embodiments, wearable devices are not locked and may be removed at the discretion of their users.

In an embodiment, wearable device 300 includes integrated input/output circuitry 360 which includes audio module 361, gesture module 362, beacon module 363, power module 364, surveillance module 365, video module(s) 366, authentication module(s) 367, user interface module 368, and biometric module 369. Audio module 361 can include circuitry for receiving and transmitting audio such as a microphone and speakers.

Gesture module 362 can include circuitry for receiving touch gestures received on display 340 and translating the touch gestures to commands and/or instructions for controlling wearable devices. For example, a touch gesture received in the context of a text application may be translated to a specific letter. Gesture module 362 may perform the translation and issue an instruction for displaying the specific letter on display 340.

Beacon module 363 can include circuitry for communicating with access points (or beacons) distributed in various locations of the controlled environment. Beacons and their functionality are discussed in further detail with respect to FIGS. 7A-7D. Power module 364 can include circuitry for providing power to wearable device 300. For example, power module 364 can be implemented as a rechargeable battery. In some embodiments, power module 364 is a wireless rechargeable battery which can be recharged through a variety of methods including inductive charging and radio-frequency (RF) charging. Inductive charging includes power module 364 receiving electromagnetic fields and converting the received electromagnetic fields into energy to charge or power wearable device 300. For example, wearable device 300 having a power module 364 that is charged through inductive charging may be placed on an inductive charging pad. RF charging includes power module 364 receiving signals such as radio-frequency signals and converting the signals into power for use by wearable device 300. In some embodiments, such as when wearable device is inserted into a body of the user, power module 364 can be a blood battery electrolyte module that relies on electrolytes in the blood to generate power for wearable device 300. In some embodiments, power module 364 is a rechargeable battery that is charged through a physical connection to wearable device 300. For example, a charging cable or connector that is connected to a power outlet can be attached to wearable device 300 that supplies a charge to power module 364.

Surveillance module 365 can include circuitry that enables remote activation and remote control of the surveillance functionality of wearable device 300 (e.g., a surveillance mode). For example, when receiving an appropriate signal from a monitoring center and/or authorized personnel such as through communication interface 330, surveillance module 365 activates the appropriate components of wearable device for conducting the requested surveillance. For example, the authorized personnel may request that wearable device 300 begin recording audio. Based on the request, surveillance module 365 can activate audio module 361 which can include a microphone and initiate recording of ambient sounds from the surrounding physical environment based on the received signal from authorized personnel. Conversely, the signal to begin surveillance may be provided through wearable device 300 such as through a gesture or command from a user of wearable device 300. For example, the user may initiate a biometric surveillance feature such as recording the user's heart rate or oxygen levels through an application on wearable device 300. In response, surveillance module 365 may activate biometric module 369 and begin recording the requested biometric information of the user. Moreover, in some embodiments, surveillance module 365 can operate in the background without providing any indication to the user of the wearable device that surveillance functionality has been activated. In some embodiments, the monitoring center activates the surveillance mode which results in activating the appropriate modules as a group as discussed above. In some embodiments, the monitoring center can activate individual modules, such as audio module 361 or biometric module 369, separately. Surveillance module 365 can also include circuitry that enables remote deactivation of the surveillance functionality of wearable device 300. In some embodiments, monitoring center and/or authorized personnel can send a signal to remotely deactivate the surveillance mode, which results in deactivating corresponding modules as a group, or can send a signal that remotely deactivates individual modules.

Video module(s) 366 can include circuitry for receiving and transmitting video such as a camera. The camera is utilized for capturing visual information regarding the physical environment being viewed by a user of wearable device 300. Information from the camera is provided to communication center for processing by communication center 220.

Authentication module 367 can include circuitry for ensuring that the user of the wearable device is allowed to use wearable device. Authentication module 367 can utilize username/password, voice signatures, fingerprints, retinal or iris information, and facial information to verify the identity of the user. For example, authentication module 367 can interact with audio module 361 to receive a user's voice information, video module 366 to receive a user's iris or facial information, and/or biometric module 369 to receive a user's heartbeat or fingerprint information. Authentication module 367 can also include circuitry for verifying commands or instructions received from authorized personnel.

User interface module 368 can include circuitry for controlling dynamic user interfaces displayed by wearable device 300 on display 340 and/or by holographic projector 341. User interface module 368 can customize and modify dynamic user interfaces based on a user of wearable device 300, the location of wearable device 300, and based on signals received from authorized personnel. User interface module 368 is responsible for the dynamic user interface of wearable device 300. As will be discussed further below with respect to FIGS. 4A-4D and FIGS. 7A-7D, the user interface of wearable device 300 dynamically adapts based on user information, wearable device location, and any other information such as administrator rules. Accordingly, user interface module 368 provides a dynamic user interface for wearable device 300.

Biometric module 369 can include circuitry for receiving and tracking biometric information from a user of wearable device 300 such as a heart rate monitor, oxygen level detector, and fingerprint detector. Biometric information may be provided to authentication subsystem 216 for processing.

Exemplary Wearable Device Operation

Exemplary usage of wearable device 300 in a controlled environment will be described with respect to FIGS. 4A-4D, 5, and 6. The exemplary usage described in FIGS. 4A-4D, 5, and 6 can be performed by processing logic that can comprise hardware (e.g., circuitry, dedicated logic, programmable logic, microcode, etc.), software (e.g., instructions executing on a processing device), or a combination thereof. For illustrative purposes, FIGS. 4A-4D, 5, and 6 are described with respect to FIGS. 1-3 but are not limited to these example embodiments. For example, FIGS. 4A-4D, 5, and 6 is described with respect to wearable device 300 of FIG. 3 but may apply to any of wearable devices 121A-121C of FIG. 1.

Figure 4A:
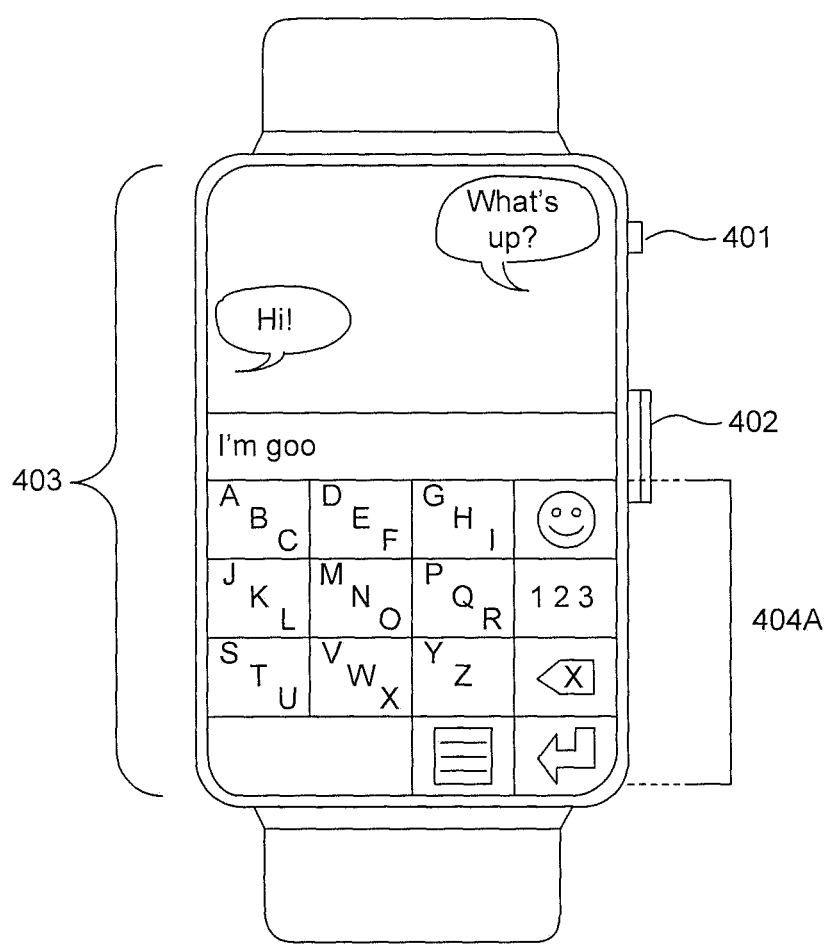
FIG. 4A illustrates a wearable device having an exemplary interface for use in the exemplary wearable device communication system of FIG. 1, according to embodiments of the present disclosure.

FIG. 4A illustrates exemplary wearable device 400A which includes a power button 401, a scroll/select mechanism 402, and a display 403. Scroll/select mechanism 402 can be used as a physical mechanism for controlling a dynamic user interface on display 403. For example, scroll/select mechanism 402 can be implemented as a wheel that a user can rotate up and down. In some embodiments, rotating scroll/select mechanism 402 upward moves a cursor up within the dynamic user interface. Similarly, rotating scroll/select mechanism 402 downward moves a cursor down within the dynamic user interface. In some embodiments, scroll/select mechanism 402 may also be a button that can be depressed to activate a context-sensitive command (e.g., to select a highlighted icon or link).

Display 403 is a capacitive or resistive touchscreen display that is capable of receiving touch inputs from a user's finger and/or touch implement such as a stylus. In some embodiments, display 403 displays an input interface 404A such as a keyboard that allows a user of wearable device 400A to input information. Input interface 404A may comprise any number of software icons that correspond to inputs that may be selected by a user. For example, when implemented as a keyboard, input interface 404A displays alphanumeric keys. Wearable device 400A may adjust a display setting, a configuration setting, and the input type of input interface 404A based on a number of factors including a user profile and/or administrative rules. Examples of a display setting include but are not limited to colors and size of the software keys or letters of input interface 404A. An example of a configuration setting include but not limited to the layout of input interface 404A. The layout of input interface 404A includes arrangement of the software keys and letters. Examples of input types include keyboards and gesture areas as will be discussed in further detail with regard to FIGS. 4B-4D.

Figure 4B:
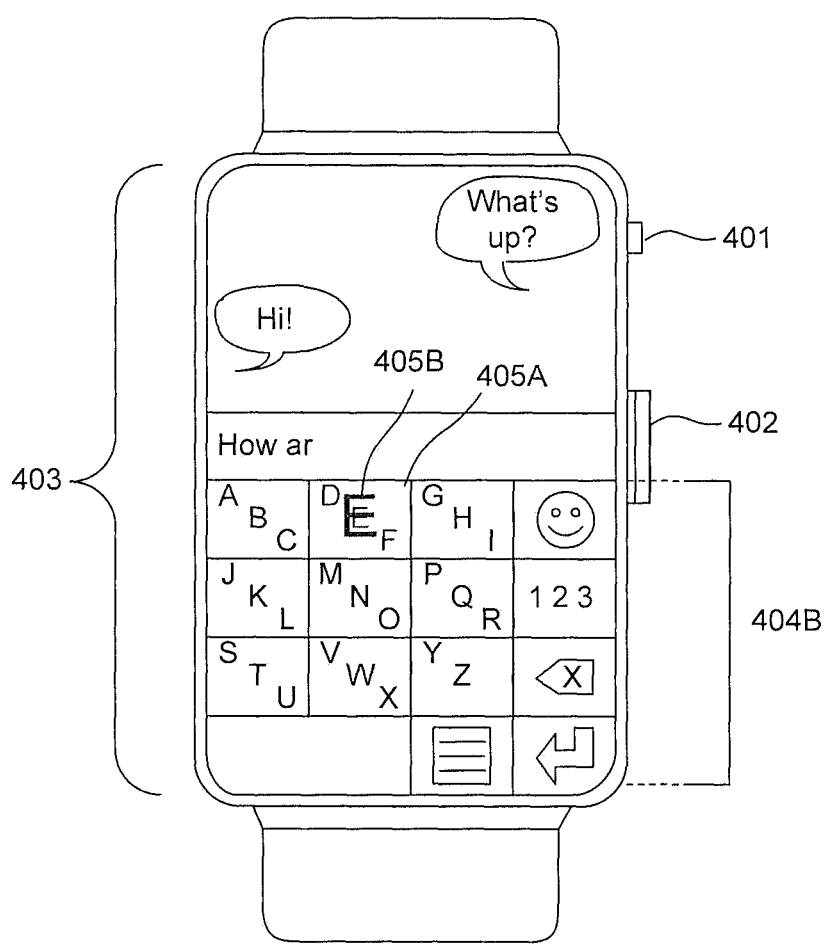
FIG. 4B illustrates a wearable device having another exemplary interface for use in the exemplary wearable device communication system of FIG. 1, according to embodiments of the present disclosure.

FIG. 4B illustrates exemplary wearable device 400B having display 403 displaying input interface 404B. Software keys of input interface 404B has been customized to display an emphasized letter 405B that the user wishes to select. In some embodiments, a user of wearable device 400B selects the "F" of input interface 404B by performing three successive short presses of software key 405. In some embodiments, a short press is a touch of a predetermined period of time (e.g., less than 2 seconds). In some embodiments, the time between each successive short press is a second predetermined period of time (e.g., less than 2 seconds). A first short press of software key 405A selects "D"; a second short press of software key 405A within a predetermined period of time after the first short press selects "E"; and a third short press of software key 405A within a predetermined period of time after the second short press selects "F." In some embodiments, each short press of software key 405A results in displaying emphasized letter 405B. User of wearable device 400B may send the displayed emphasized letter 405B (e.g., "E") to an application (e.g., messaging application) by long pressing software key 405.

Figure 4C:
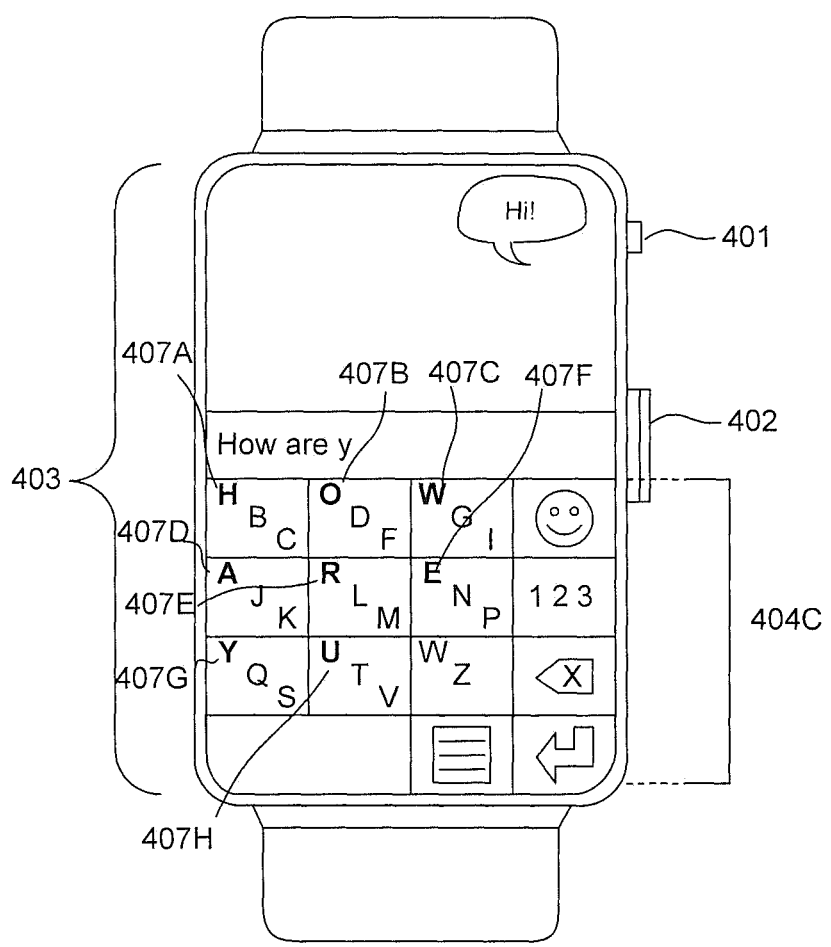
FIG. 4C illustrates a wearable device having another exemplary interface for use in the exemplary wearable device communication system of FIG. 1, according to embodiments of the present disclosure.

FIG. 4C illustrates exemplary wearable device 400C having display 403 display input interface 404C. Input interface 404C has a different display setting and a different configuration setting than input interface 404A. A component of wearable device 400C, such as user interface module 368, can modify display and configuration settings of input interface 404C based on a user profile the current application displayed on display 403, and/or a context of wearable device 400C. For example, wearable device 400C can have access to a user's most frequently used phrases or letters based on the user's history with wearable device. This user information can be stored in user interface module 368 and/or in wearable profile device subsystem 214 of communication center 200. For example, if user starts an application, wearable device 400C may retrieve the user profile which contains information regarding the user's typing habits such as the user's typing history and the user's most used phrases and letters. In some embodiments, the user profile can also include information that associates the user information with applications of wearable device 400C. For example, the user profile can store a user's typing habits in an messaging application, the user's typing habits in a browsing application, and the user's typing habits in a telephone application. Accordingly, in some embodiments, when the user starts a messaging application, wearable device 400C may adjust a configuration setting such as an arrangement of the letters of input interface 404C to emphasize the user's most used letters for the messaging application. In this manner, input interface 404C provides a dynamic interface that changes based on the user's habits, user's preferences, and the application in which the user is currently interacting. For example, the user profile may indicate that the user types "How are you" frequently in a messaging application and wearable device 400C may customize input interface 404C to emphasize each letter 407A, 407B, 407C, 407D, 407E, 407F, 407G, and 407H of the frequently used phrase. In another application, the user profile could indicate another most frequently used phrase, and input interface 404C could dynamically change the configuration of the alphanumeric keys based on the user profile.

Wearable device 400C may also adjust a display setting such as bolding the first letter of each software key to emphasize the user's most used letters 407A, 407B, 407C, 407D, 407E, 407F, 407G, and 407H for the messaging application. In other embodiments, wearable device 400C may customize settings of the input interface 404C based on a context of wearable device 400C. Context can include but is not limited to a location, a certain mode, and/or a signal received from a communication center.

Figure 4D:
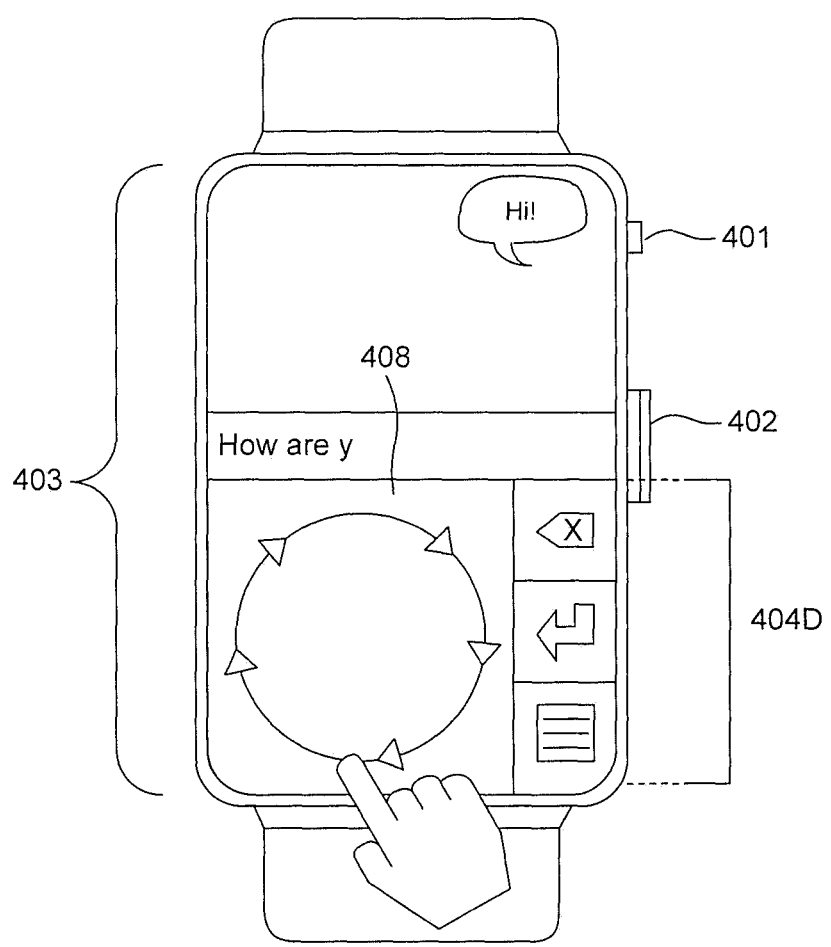
FIG. 4D illustrates a wearable device having another exemplary interface for use in the exemplary wearable device communication system of FIG. 1, according to embodiments of the present disclosure.
Figure 4E:
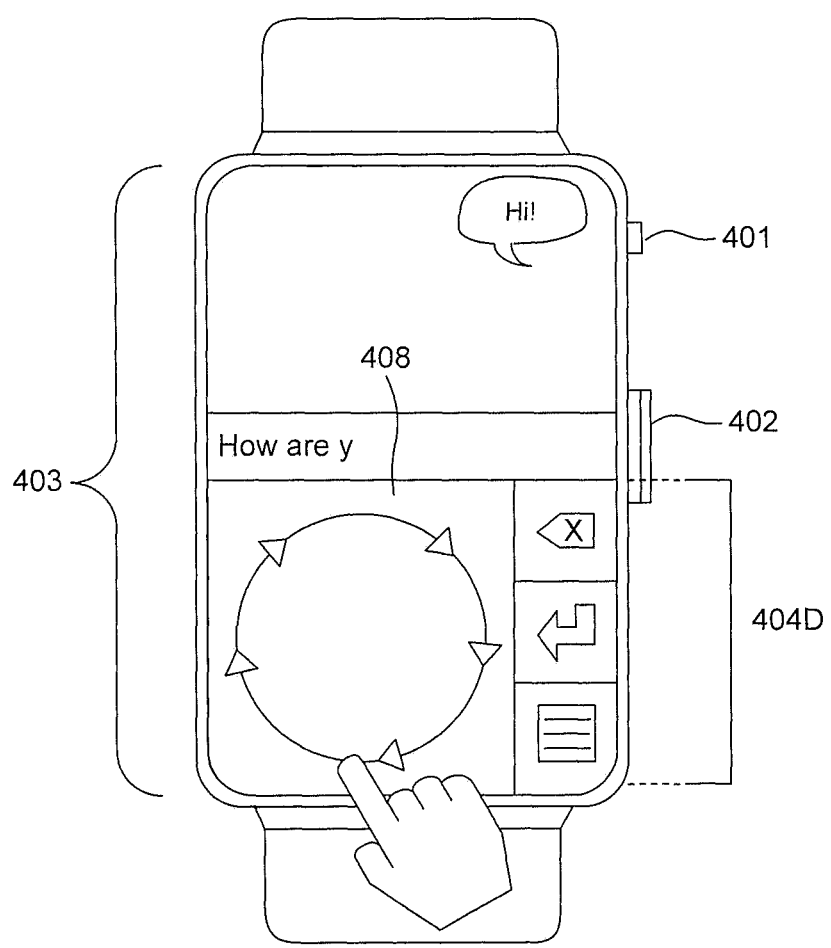

FIG. 4D illustrates exemplary wearable device 400D having display 403 display input interface 404D. Input interface 404D can include a gesture area 408 for receiving touch input from a user of wearable device 400D. Input interface 404D has a different input type than input interfaces 404A-C. The user can provide touch gestures in gesture area 408. A component of wearable device 400D, such as gesture module 362, translates gestures received through gesture area 408 into a corresponding command or instruction, such as a specific letter corresponding to the touch gesture. For example, gesture module 362 translates a circular motion received in gesture area 408 into the letter "O." In some embodiments, gestures are associated with the particular application currently displayed on display 403. For example, gesture module 362 translate the circulation motion into the letter "O" for a messaging application but into a command for repeating a song in a media application.

Figure 5:
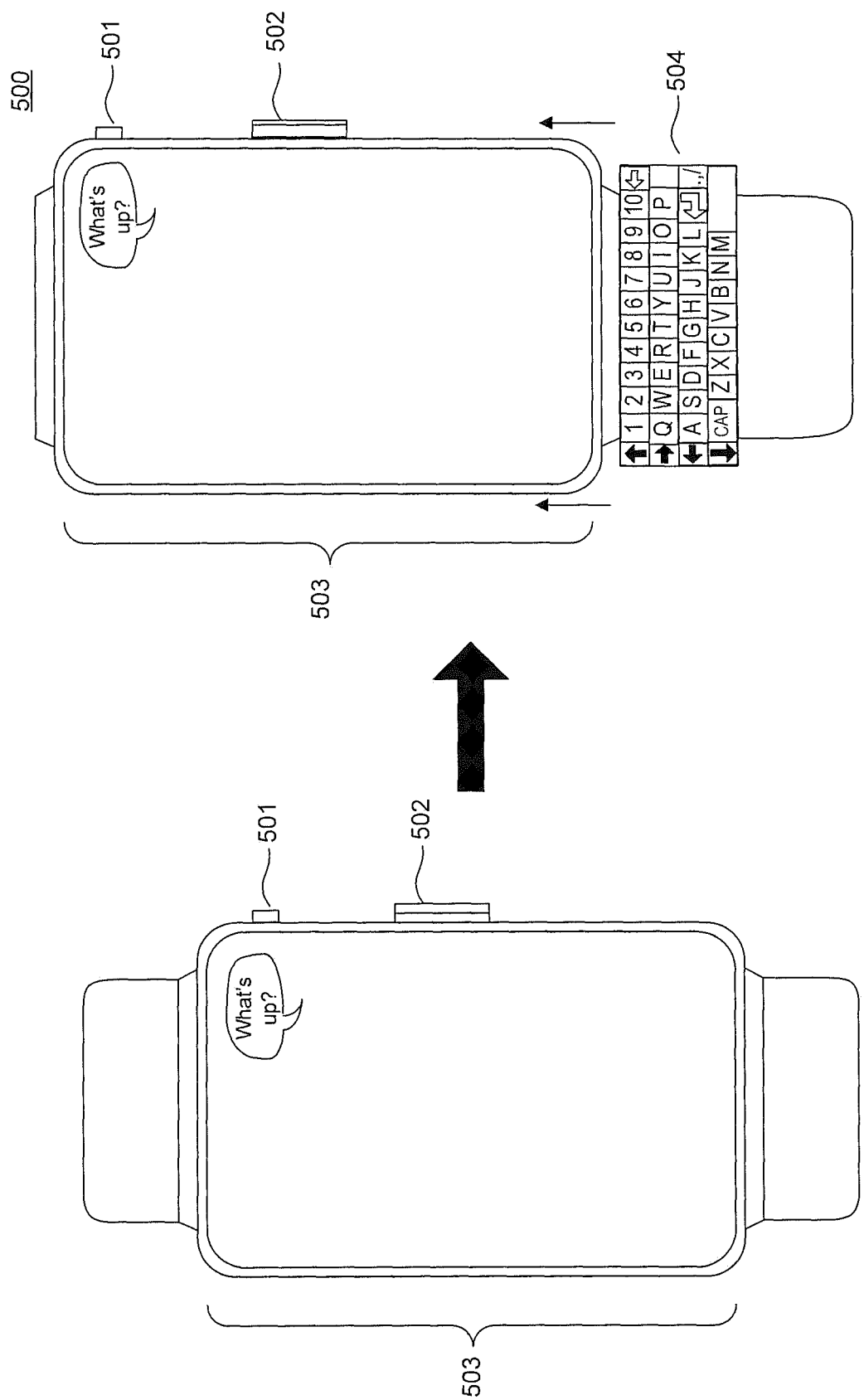
FIG. 5 illustrates a wearable device having an exemplary physical interface for use in the exemplary wearable device communication system of FIG. 1, according to embodiments of the present disclosure.

FIG. 5 illustrates exemplary wearable device 500 which includes a power button 501, a scroll/select mechanism 502, and a display 503. Scroll/select mechanism 502 operates similarly to scroll/select mechanism 402 as discussed above with respect to FIGS. 4A-4D. Display 503 may situated on a sliding mechanism (not shown) that allows a user or wearable device 500 to move display 503 a predetermined distance upward. Physical keyboard 504 can be situated underneath display 503 such that physical keyboard 504 is revealed when display 503 is moved upward the predetermined distance upward. Physical keyboard 504 can be implemented having any number of physical keys that allows the user to provide inputs to applications on wearable device 500. In some embodiments, physical keyboard 504 can be implemented as a QWERTY style keyboard.

Figure 6:
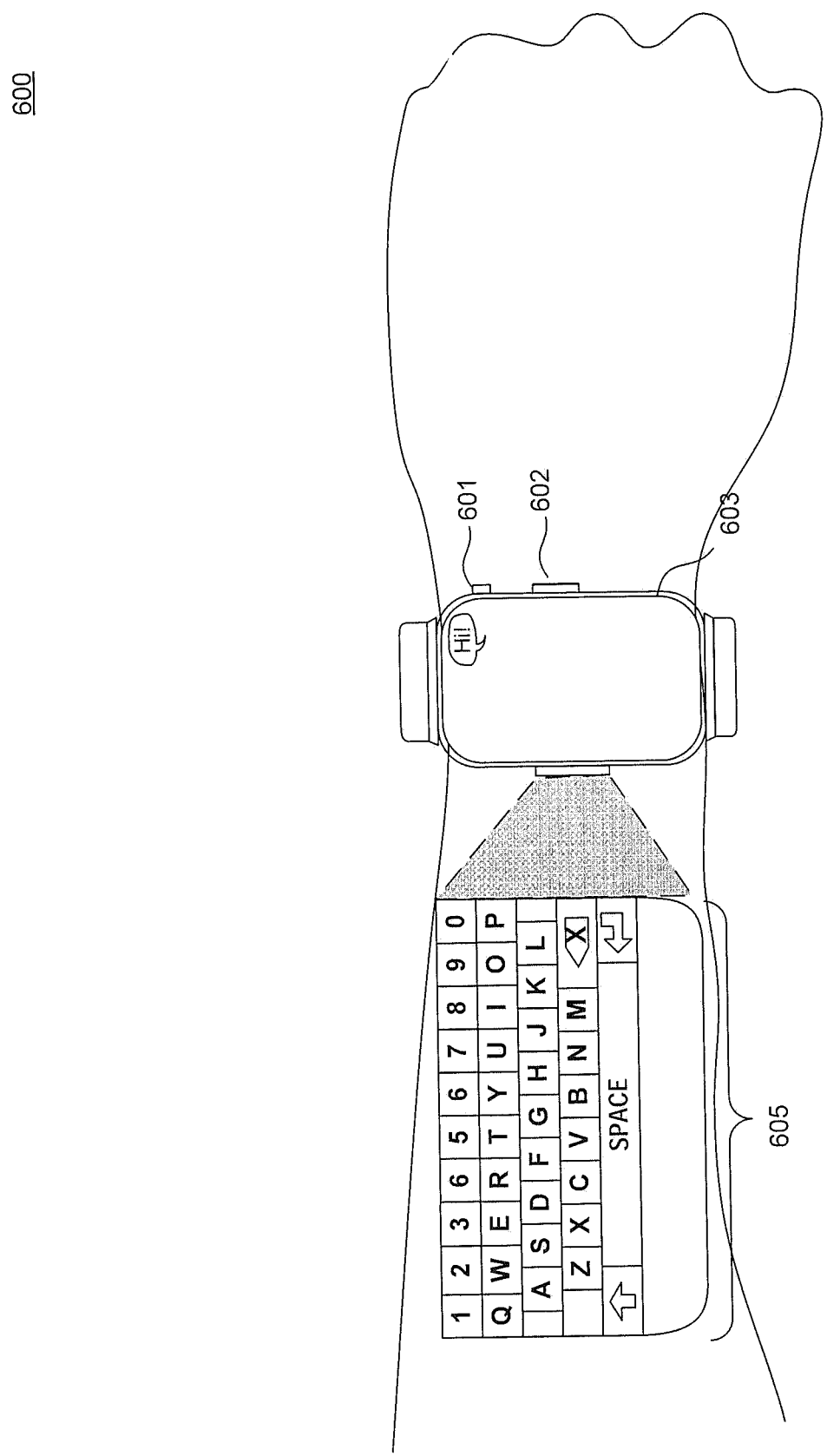
FIG. 6 illustrates a wearable device having an exemplary virtual interface for use in the exemplary wearable device communication system of FIG. 1, according to embodiments of the present disclosure.

FIG. 6 illustrates exemplary wearable device 600 which includes power button 601, a scroll/select mechanism 602, display 603, and holographic projector 604. In some embodiments, holographic projector 604 projects a virtual keyboard 605 onto a surface external to wearable device 600 such as the user's forearm. Holographic projector 604 also includes a fingertip detector for detecting and determining a position of the user's fingertip in relation to the virtual keyboard 605. Based on determining the user's fingertip position, a component of wearable device 600, such as user interface module 368, translates the fingertip position into a corresponding command, such as a specific letter of virtual keyboard 605. User interface module 368 can then send the translated command to an application for an appropriate action, such as displaying the specific letter on display 603.

Exemplary System Operation

Exemplary usage of wearable device communication system 100 in a controlled environment will be described with respect to FIGS. 7A-7D and 8-11, according to some embodiments. The exemplary usage described in FIGS. 7A-7D can be performed by processing logic that can comprise hardware (e.g., circuitry, dedicated logic, programmable logic, microcode, etc.), software (e.g., instructions executing on a processing device), or a combination thereof. For illustrative purposes, FIGS. 7A-7D are described with respect to FIGS. 1-3 but are not limited to these example embodiments. For example, FIGS. 7A-7D is described with respect to wearable device 300 but may apply to any of wearable devices 121A-121C.

Figure 7A:
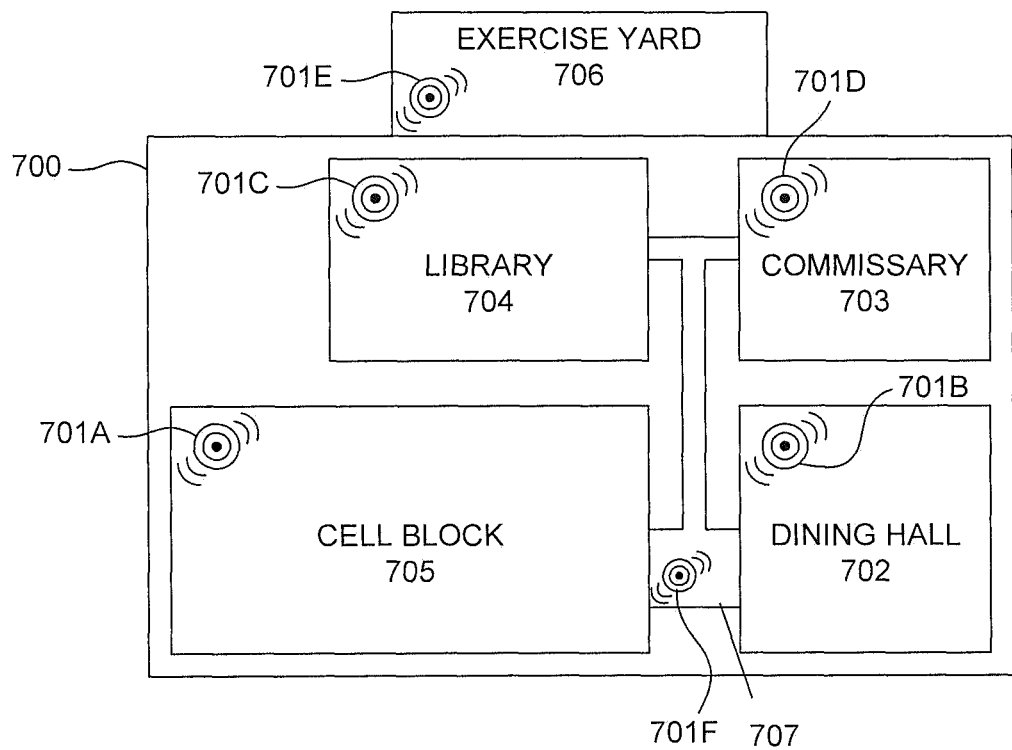
FIG. 7A illustrates a controlled environment having distributed power and/or network beacons, according to embodiments of the present disclosure.

FIGS. 7A-7D depict various dynamic user interfaces of wearable device 300 based on a location within a controlled environment 700. FIG. 7A depicts an exemplary embodiment of a controlled environment 700. In some embodiments, controlled environment 700 includes beacons or access points 701A-701E. Beacons 701A-701E are distributed throughout controlled environment 700 and provide several functions to wearable devices within controlled environment 700. Functions include but are not limited to wireless networking, radio-frequency waves for providing power, and/or location determination. In some embodiments, controlled environment 700 also includes dining hall 702, commissary 703, library 704, cell block 705, exercise yard 706, and hallway 707. In some embodiments, there is a beacon in each area of controlled environment 700 such as beacon 701A in cell block 705, beacon 701B in dining hall 702, beacon 701C in library 704, beacon 701D in commissary 703, beacon 701E in exercise yard 706, and beacon 701F in hallway 707. Each beacon 701A-701F can act as an access point and provide a wireless network connection to any wearable devices located in the same area as beacon 701A-701F.

Figure 7B:
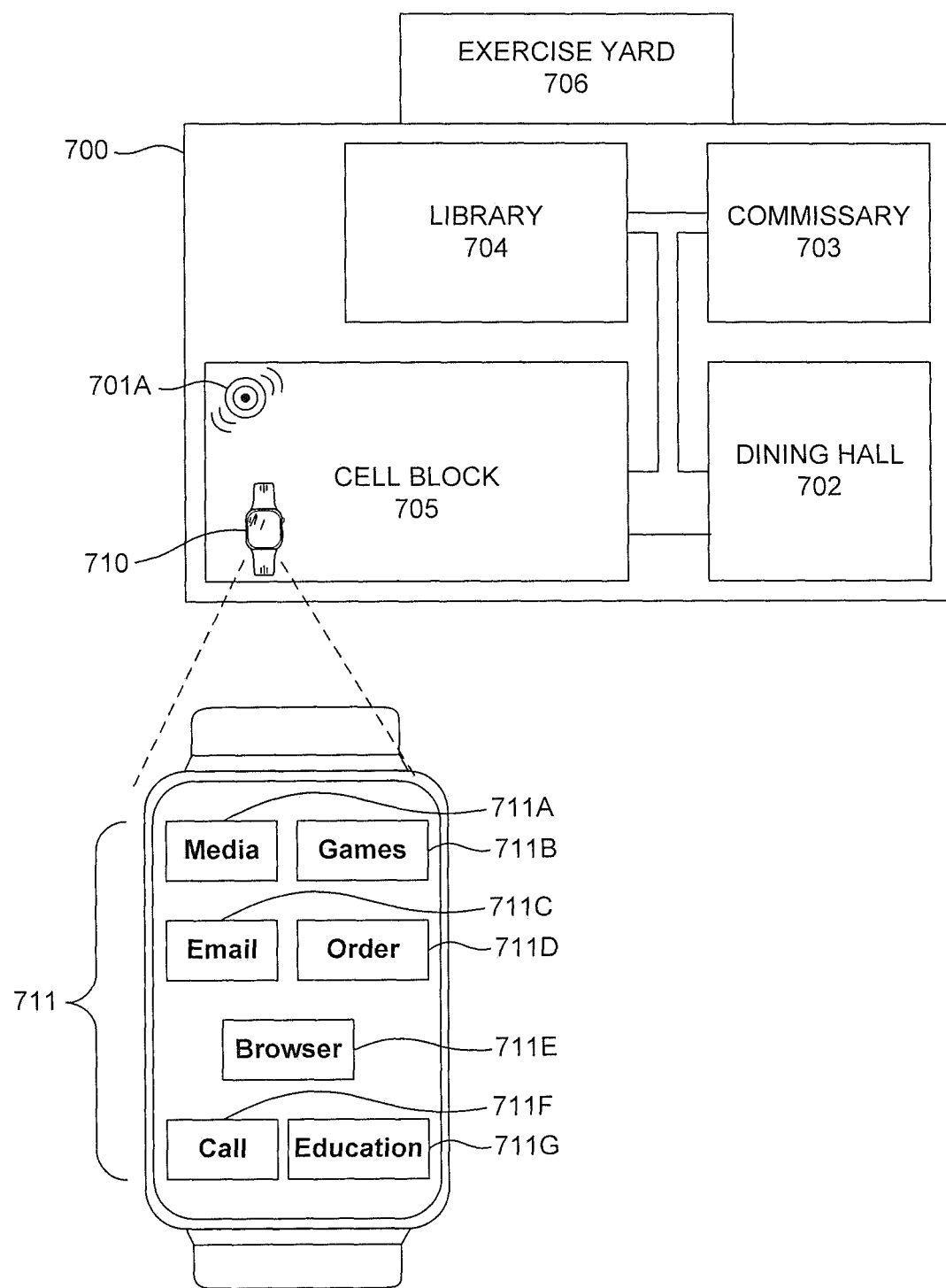
FIGS. 7B-7D illustrate a wearable device having an exemplary interface customized for use in different locations of the controlled environment of FIG. 5A, according to embodiments of the present disclosure.

FIG. 7B depicts an exemplary embodiment of controlled environment 700 with a wearable device 710 located near beacon 701A in cell block 705. In some embodiments, applications 711A, 711B, 711C, 711D, 711E, 711F, and 711G are displayed on display 711 of wearable device 710 based on wearable device 710 being located within cell block 705. For example, beacon 701A detects wearable device 710 and provides information regarding wearable device 710, such as wearable device 710's location in cell block 705, to a monitoring center, such as monitoring center 140. Wearable device 710 may customize functionality based on its location such as through beacon module 363 or based on a remote signal from a monitoring center. The remote signal can be based on any number of factors including a user profile of the user of wearable device 700, the location of wearable device 700, a certain time of day, and/or administrator's preferences. Examples of customizing functionality include providing certain applications that can be accessed through display 711 of wearable device 710. In some embodiments, controlled environment is a prison, a user is an inmate of the prison, and a user profile is an inmate profile.

For example, wearable device 710 in cell block 705 permits a user to access applications 711A, 711B, 711C, 711D, 711E, 711F, and 711G. This permission can be based on any number of factors including but not limited to the user's profile and/or administrative rules associated with the user and/or area of controlled environment 700. In some embodiments, a user's profile indicates the applications to which the user has access through a wearable device. Wearable device 710 can first verify that any administrative rules are authentic (e.g., received from authorized personnel of controlled environment 700). For example, wearable device 710 can confirm that administrative rules have an appropriate signature or decrypt the administrative rules using a private key provided to wearable device 710 by controlled environment 710. In some embodiments, administrative rules indicate the applications that are allowed for a particular user and/or in a particular area of controlled environment 700. For example, an administrative rule can indicate that all applications are accessible when wearable device 710 is located within cell block 705. This rule can be applied to a particular user or all users. Based on the administrative rule for cell block 705, a component in wearable device 710, such as user interface module 363, can modify the dynamic user interface to allow a user access to the available applications. The administrative rule can be specific to the user of wearable device 710 or can be applied to all users. For example, one user may allowed to use all available applications while in his cell block while another user may be restricted to only certain applications while in his cell block.

Figure 7C:
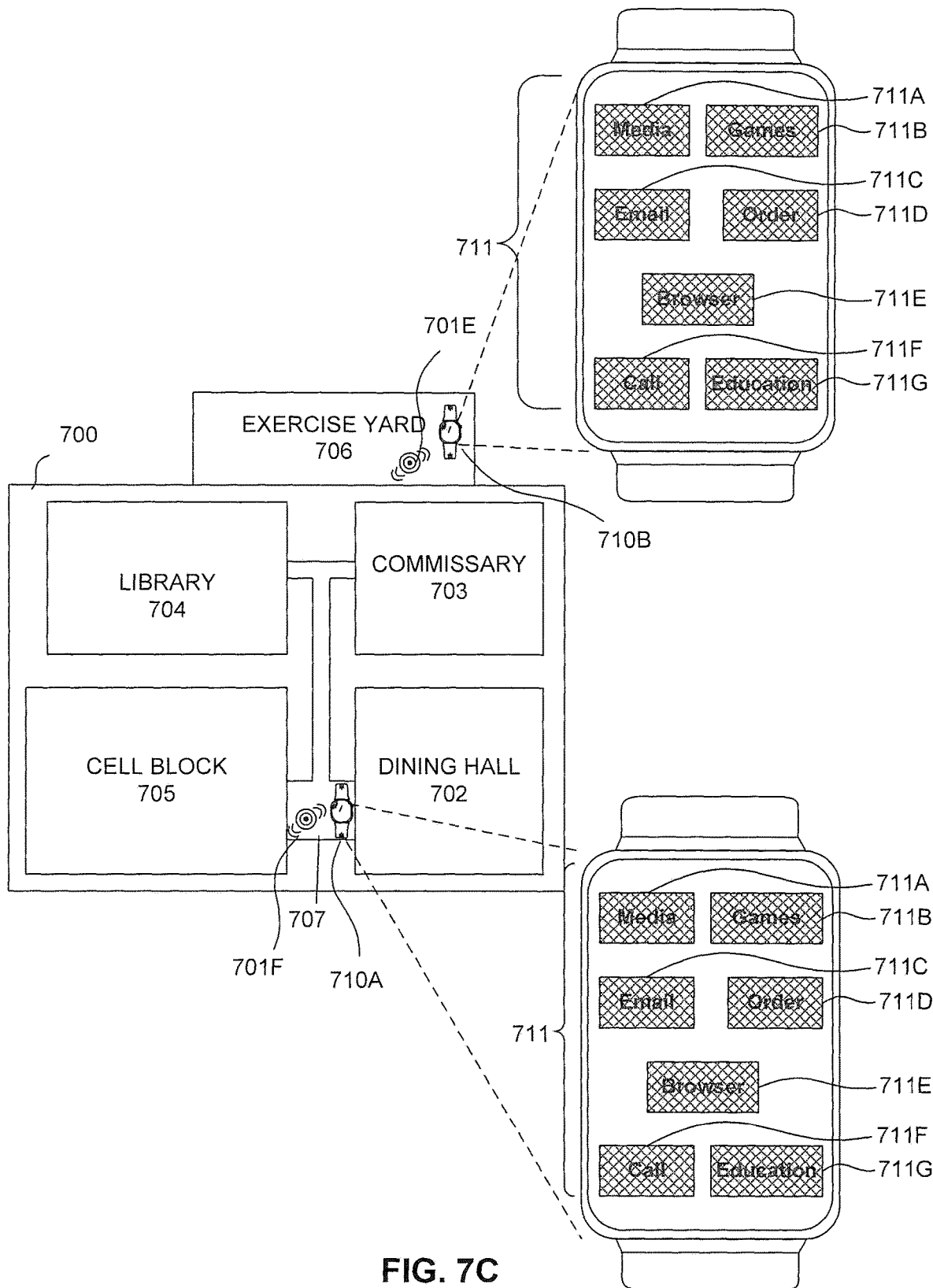

FIG. 7C depicts an exemplary embodiment of controlled environment 700 with a wearable device 710A located near beacon 701F in hallway 707 and wearable device 710B located near beacon 701E in exercise yard. Based on user profiles for the users of wearable devices 710A and 710B and/or administrative rules associated with the areas of controlled environment 700, wearable devices 710A and 710B determine that its users are not allowed to access any applications. Accordingly, a component of wearable devices 710A and 710B, such as user interface module 363, modifies the applications 711A, 711B, 711C, 711D, 711E, 711F, and 711G on display 711 such that a user cannot select any application while wearable devices 710A and 710B are determined to still located in hallway 707 and exercise yard 706, respectively. For example, wearable devices 710A and 710B may remove applications from being displayed or grey out applications to indicate that the applications are not available.

Figure 7D:
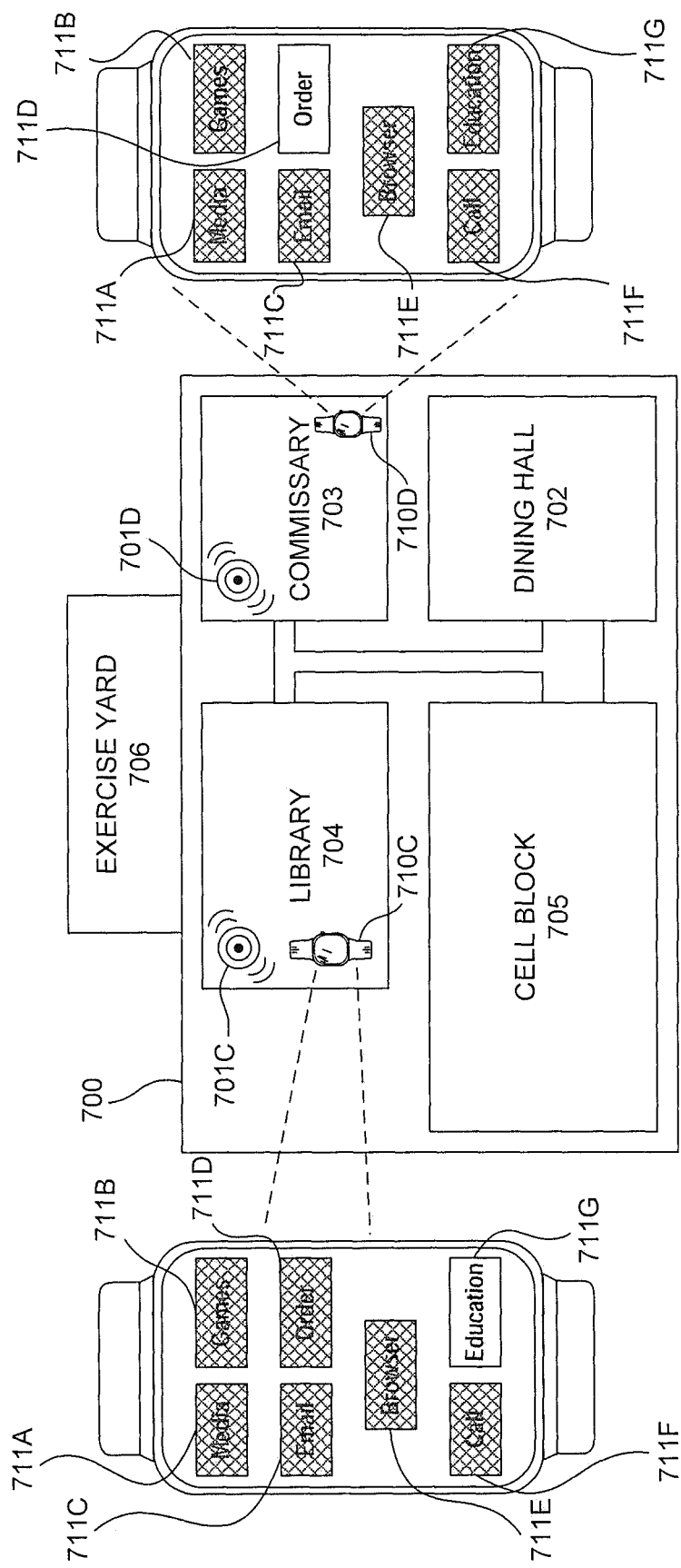

FIG. 7D depicts an exemplary embodiment of controlled environment 700 with a wearable device 710C located near beacon 701C in library 704 and a wearable device 710D located near beacon 701D in commissary 703. Based on user profiles for the users of wearable devices 710C and 710D and/or administrative rules associated with the users and/or particular locations, wearable devices 710C and 710D modify the applications that can be selected by their respective users. For example, based on a user profile for the user of wearable device 710C and/or administrative rules associated with the user and/or library 704, wearable device 710C determines that only "Education" application 711G is accessible while wearable device 710C is located in library 704. Based on this determination, wearable device 710C modifies the dynamic user interface to allow user to only select "Education" application 711G and prevent the user from selecting other applications 711A-F. For example, wearable device 710C may grey out applications 711A-F to indicate that the applications are not available for selection.

Based on a user profile for the user of wearable device 710D and/or administrative rules associated with the user and/or commissary 703, wearable device 710D determines that only the "Order" application 711D is accessible while wearable device 710D is located in commissary 703. Based on this determination, wearable device 710D modifies the dynamic user interface to allow user to only select "Order" application 711D and prevent the user from selecting other applications 711A-C and 711E-G. For example, wearable device 710D may grey out applications 711A-C and 711E-G to indicate that the applications are not available for selection.

Operations of operating wearable devices in a controlled environment will be described with respect to FIGS. 8-11. Although the physical devices and components that form the system have largely already been described, additional details regarding their more nuanced operation will be described below. The exemplary operations described in FIGS. 8-11 can be performed by processing logic that can comprise hardware (e.g., circuitry, dedicated logic, programmable logic, microcode, etc.), software (e.g., instructions executing on a processing device), or a combination thereof. For illustrative purposes, FIGS. 8-11 are described with respect to FIGS. 1-3 but are not limited to these example embodiments. While FIGS. 8-11 contain methods of operation for wearable devices in wearable device communication system 100, the operations are not limited to the order described below, and various operations can be performed in a different order. Further, two or more operations of each method can be performed simultaneously with each other.

Figure 8:
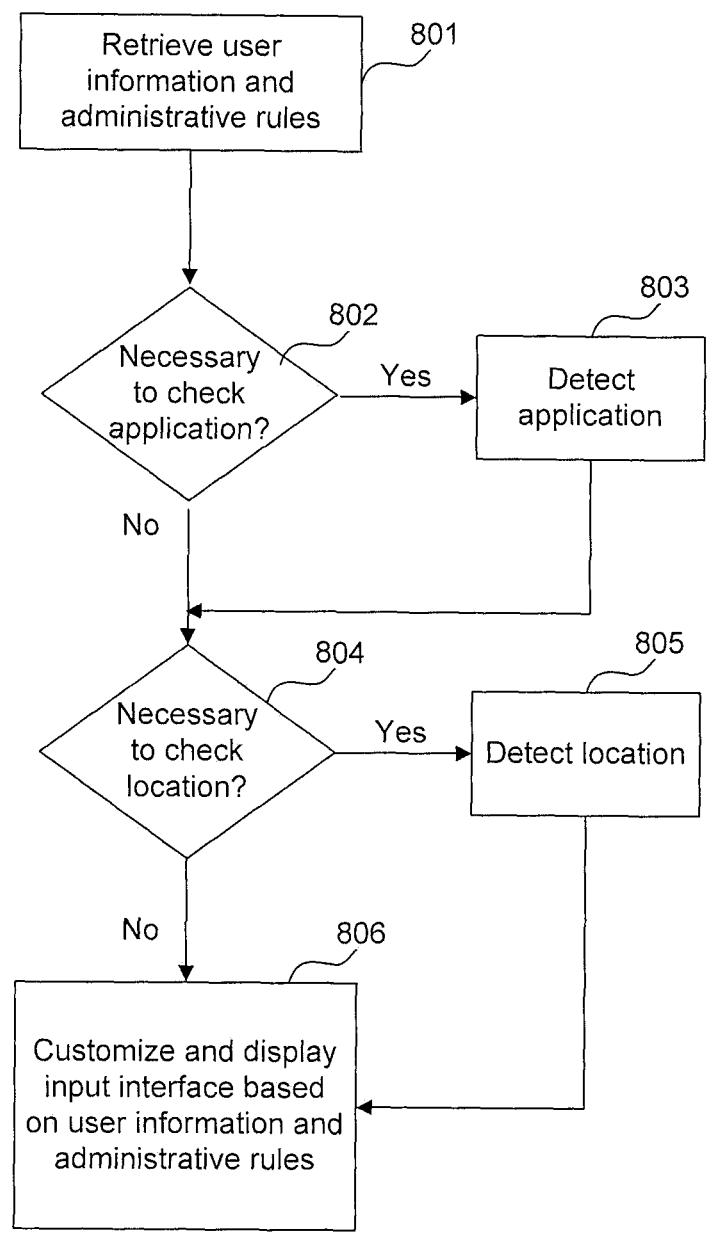
FIG. 8 illustrates a flowchart diagram of a method for customizing input interface of a wearable device for use in the exemplary wearable device communication system of FIG. 1, according to embodiments of the present disclosure.

FIG. 8 illustrates a flowchart diagram of a method 800 for customizing an input interface on a wearable device, such as wearable device 300 of FIG. 3 or wearable device 400A of FIG. 4A, according to embodiments of the present disclosure. Method 800 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 8, as will be understood by a person of ordinary skill in the art.

In 801, wearable device 300 retrieves user information, such as a user profile, and administrative rules. The user information can be the user's profile which can be located in wearable device profile subsystem 214. For example, the user information can specify the user's typing habits, typing history, most frequently used letters, most frequently used phrases, and/or applications authorized to be used by the user. The administrative rules control authorized functions that can be performed by wearable device 300 as specified by authorized personnel of the controlled environment and can be retrieved from authentication subsystem 216. For example, administrative rules can allow or restrict certain interfaces based on a specific user or all users and/or based on a location of wearable device 300. In some embodiments, retrieving administrative rules includes verifying that the administrative rules are from an authorized source, such as a monitoring center of a prison.

In some embodiments, wearable device 300 downloads administrative rules at predetermined times (e.g., 3:00 AM) or at predetermined intervals (e.g., every day). Wearable device 300 can store downloaded administrative rules in memory, such as memory 322. In addition, or alternatively, wearable device 300 can download administrative rules as needed. For example, wearable device 300 can download the appropriate administrative rule (if any), when wearable device 300 detects its location in a certain area of the controlled environment. In some embodiments, the administrative rules can be pushed to wearable device 300 at the discretion of the controlled environment. In some embodiments, wearable device 300 may be provided to users with base administrative rules already pre-loaded into memory 322. These base administrative rules can specific basic functions that can be performed by wearable device 300. Additional authorized functions can be added later through the additional administrative rules provided to wearable device 300.

In 802, wearable device 300 determines whether it is necessary to detect the application currently being used by the user and displayed on display 340. This determination is based on the retrieved user information and/or the retrieved administrative rules. For example, the retrieved user information can specify the user's preference that a virtual keyboard be customized based on the type of application so that the user may have a different virtual keyboard for different applications. If yes, in 803, wearable device 300 determines the current application being used by the user. If no, in 804, wearable device 300 determines whether it is necessary to detect its location within a specific area of the controlled environment. This determination is based on the retrieved user information and/or the retrieved administrative rules. The location detection can be based on the wearable device's 300 proximity to a beacon, based on GPS coordinates, or a combination thereof. If yes, in 805, wearable device 300 determines its current location. Alternatively, wearable device 300 may receive location information from a monitoring center, such as monitoring center 140. In 806, wearable device 300 displays an customized input interface based on the user information, administrative rules, and if applicable, the detected location of wearable device 300 and the current application.

Figure 9:
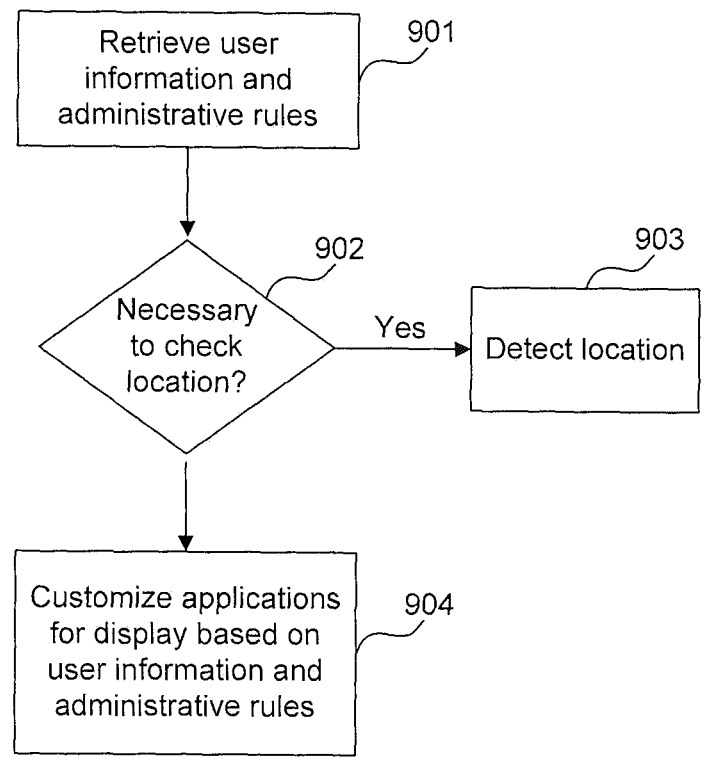
FIG. 9 illustrates a flowchart diagram of a method for customizing interface of a wearable device for use in the exemplary wearable device communication system of FIG. 1, according to embodiments of the present disclosure.

FIG. 9 illustrates a flowchart diagram of a method 900 for customizing applications wearable device, such as wearable device 300 of FIG. 3 or wearable device 400A of FIG. 4A, according to embodiments of the present disclosure. Method 900 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 9, as will be understood by a person of ordinary skill in the art.

In 901, wearable device 300 retrieves user information, such as a user profile, and administrative rules. As previously discussed, the user information can be included in the user's profile and the administrative rules control authorized functions of wearable device 300 as specified by authorized personnel which allow or restrict access to certain features of wearable device 300. For example, administrative rules can allow or restrict a specific user's access to certain applications, allow or restrict all users' access to certain applications, and allow and/or restrict access, of either a specific user or all users, to certain applications in certain locations of the controlled environment. In some embodiments, retrieving administrative rules includes verifying that the administrative rules are from an authorized source, such as a monitoring center of a prison.

In 902, wearable device 300 determines whether it is necessary to detect the location of wearable device 300. This determination is based on the retrieved user information and/or the retrieved administrative rules. For example, a retrieved administrative rule can specify location-specific functionality of wearable device 300 such as access or restricted access to certain applications. If yes, in 903, wearable device 300 detects its location. Location detection features are discussed above with respect to FIG. 8. In 904, wearable device customizes the applications that can be accessed by the user based on the user information, the administrative rules and, if applicable, the location of wearable device 300.

Figure 10:
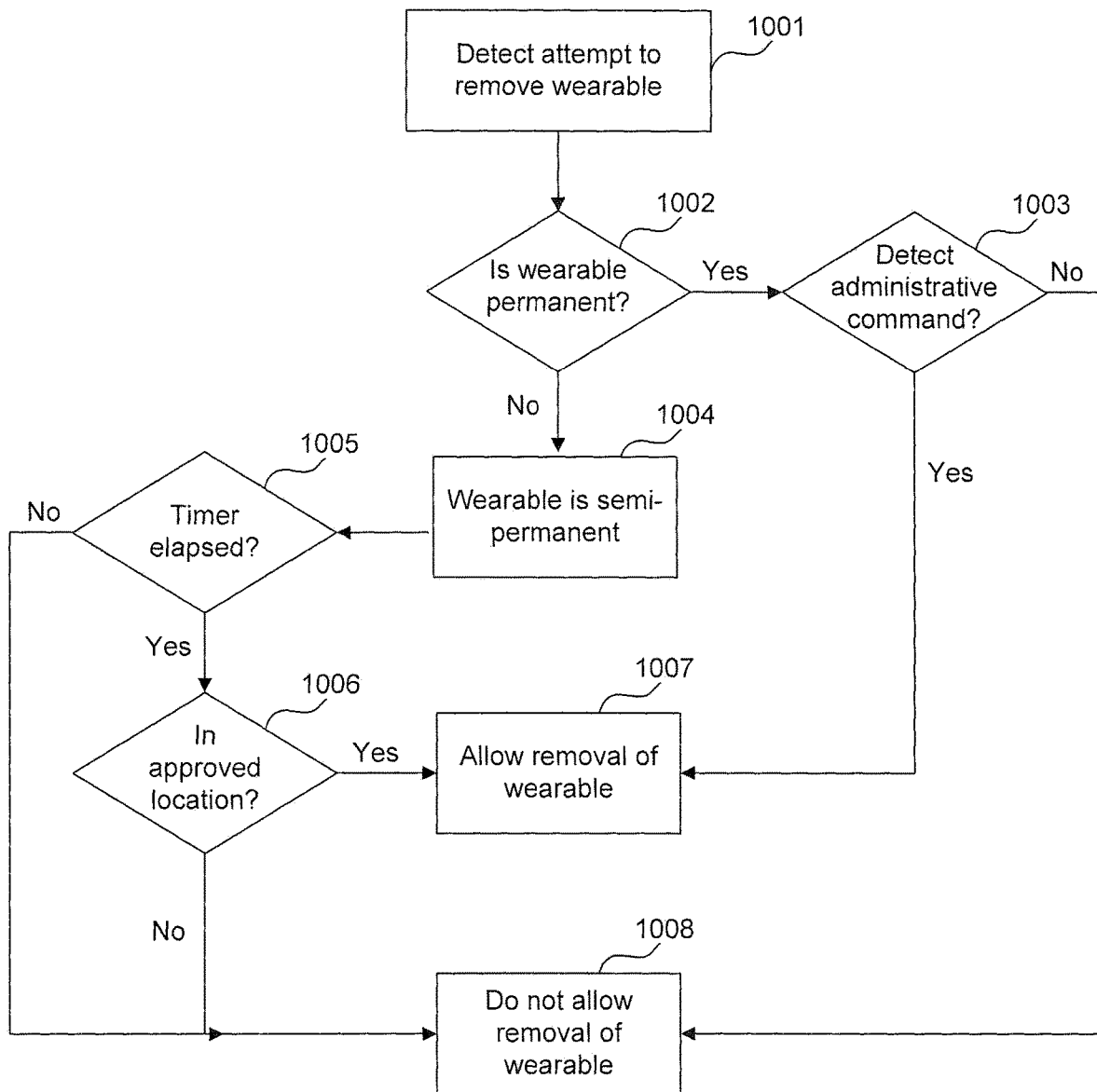
FIG. 10 illustrates a flowchart diagram of a method for determining whether to allow removal of a wearable device, according to embodiments of the present disclosure.

FIG. 10 illustrates a flowchart diagram of a method 1000 for removal of wearable device, such as wearable device 300 of FIG. 3 or wearable device 400A of FIG. 4A, from a user according to embodiments of the present disclosure. Method 1000 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 10, as will be understood by a person of ordinary skill in the art.

In 1001, wearable device 300 detects an attempt by the user to remove wearable device 300. Wearable device 300 can transmit a signal indicating the removal attempt to monitoring center 140. In 1002, wearable device 300 determines whether it is classified as a permanent wearable. As discussed above, a permanent wearable is a wearable device that cannot be removed by the user of the wearable device and is permanently attached to the user unless removed by authorized personnel of the controlled environment. If yes, wearable device 300 determines whether any administrative command is detected. An administrative command can include but is not limited to a remote signal that is received over a network or a signal from a physical device located proximate to wearable device 300 (e.g., an RF key fob). If there is no administrative command, locking module 350 of wearable device 300 does not allow the user to remove wearable device 300 at 1008. If there is an administrative command, locking module 350 allows the user to remove wearable device 300 at 1007.

If wearable device 300 is not permanent, then wearable device 300 is considered to be a semi-permanent wearable at 1004. In a controlled environment, wearable devices are not generally allowed to be removed by the users (e.g., inmates) within the controlled environment. Accordingly, in some embodiments, wearable device 300 is either permanently or semi-permanently attached to the user. In 1005, wearable device 300 next determines whether a locking timer has elapsed. A locking timer indicates a predetermined time in which wearable device 300 must be attached to the user. For example, a locking timer that specifies 10 hours indicates that wearable device 300 must be attached to the user for 10 hours before wearable device 300 can be removed. In some embodiments, an administrator or monitoring center can remotely set a specific time for the locking timer of each wearable device in the controlled environment.

If the timer has elapsed, wearable device 300 next determines whether it is located in an approved location at 1006. For example, users can be restricted to removing wearable devices only in certain locations such as the user's specific cell block. Approved locations can be specified in the user's profile and/or by an administrative rule. If the locking timer has elapsed and wearable device 300 is located in an approved location, then wearable device 300 allows the user to remove wearable device 300 at 1007. If neither condition is met, locking module 350 of wearable device 300 does not allow the user to remove wearable device 300 at 1008.

Figure 11:
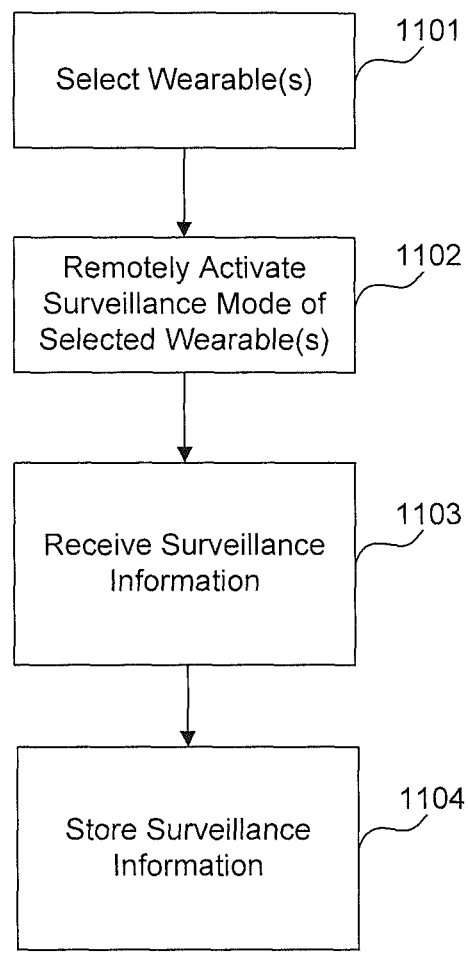
FIG. 11 illustrates a flowchart diagram of a method of conducting surveillance using wearable devices in the exemplary wearable device communication system of FIG. 1, according to embodiments of the present disclosure.

FIG. 11 illustrates a flowchart diagram of a method 1100 for activating a surveillance mode for a wearable device, such as wearable device 300 of FIG. 3 or wearable device 400A of FIG. 4A, according to embodiments of the present disclosure. Method 1100 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 11, as will be understood by a person of ordinary skill in the art.

In 1101, an administrative computer, such as monitoring center 140, selects at least one wearable device within the controlled environment. The administrative computer can allow for selection of the wearable device through a dynamic user interface that displays all wearable devices within the controlled environment as icons in the dynamic user interface. In some embodiments, authorized personnel can select each wearable device by clicking on the corresponding icon. In some embodiments, selection of wearable devices may be accomplished through administrative rules. Monitoring center 140 may push or otherwise transmit administrative rules that automatically trigger surveillance modes based on certain conditions as determined by wearable devices. For example, an administrative rule can specify that a wearable device associated with a user, who is known to have a heart or medical condition, of the controlled environment should activate a biometric mode of the wearable device when the wearable device (and therefore the user) is determined to be in the exercise yard. As another example, an administrative rule can specify that a wearable device associated with another user, who is suspected to be discussing illegal activity with fellow users, should activate an environmental mode to record ambient sounds, when the wearable device is determined to be near other wearable devices or in the dining area.

In 1102, the administrative computer remotely activates a particular surveillance mode in the selected wearable deices. In some embodiments, as discussed above, remotely activating wearable devices includes the transmission of appropriate administrative rules that control the surveillance modes of the selected wearable devices. In some embodiments, surveillance mode includes but is not limited to biometric surveillance of the user and environmental surveillance. Biometric surveillance includes activating components of wearable device 300, such as surveillance module 365 and biometric module 369, for monitoring, recording, and transmitting biometric information of the user. Biometric surveillance includes but is not limited to monitoring heart rate information, oxygen levels, and temperature of the user. Wearable device 300 can then transmit biometric information to a remote application, such as a telemedicine application located at a monitoring center. Environmental surveillance includes activating components of wearable device 300, such as audio module 361, surveillance module 365, and video module 366, for monitoring, recording, and transmitting environmental information surrounding wearable device 300. Environmental surveillance includes but is not limited to audio recordings, video recordings, and a temperature of the area of controlled environment in which wearable device 300 is located.

In 1103, the administrative computer receives surveillance information from the selected wearable devices depending on the activated surveillance mode. For example, the administrative computer will receive biometric information regarding users of selected wearable devices if biometric surveillance is activated and/or environmental information regarding a physical environment surrounding the selected wearable devices if environmental surveillance mode is activated. In 1104, the administrative computer stores the received surveillance information in a database, such as in database 222. Surveillance information may then be later analyzed by software, by authorized personnel, or used to monitor the controlled environment. In some embodiments, the stored biometric information may be transmitted to another external party such as a doctor which would allow the user to receive remote diagnosis based on his biometric information. In some embodiments, the administrative computer may then deactivate the mode which results in deactivating the modules. Alternatively, wearable device 300 may continue operating with the modules activated.

Exemplary Computer Implementation

It will be apparent to persons skilled in the relevant art(s) that various elements and features of the present disclosure, as described herein, can be implemented in hardware using analog and/or digital circuits, in software, through the execution of computer instructions by one or more general purpose or special-purpose processors, or as a combination of hardware and software.

Figure 12:
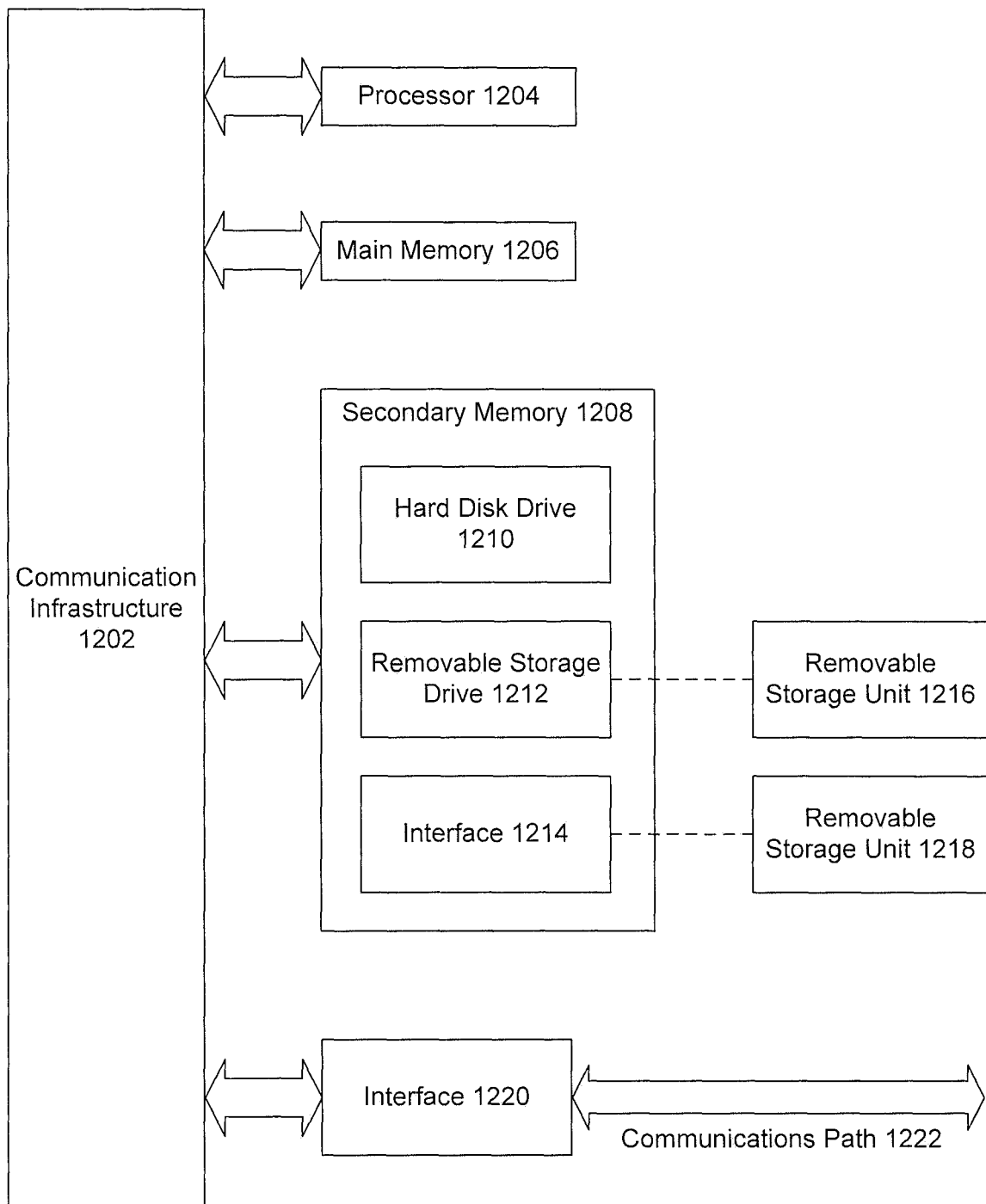
FIG. 12 illustrates a block diagram of a general purpose computer that may be used to perform various aspects of the present disclosure.

The following description of a general purpose computer system is provided for the sake of completeness. Embodiments of the present disclosure can be implemented in hardware, or as a combination of software and hardware. Consequently, embodiments of the disclosure may be implemented in the environment of a computer system or other processing system. For example, the methods of FIGS. 8-11 can be implemented in the environment of one or more computer systems or other processing systems. An example of such a computer system 1200 is shown in FIG. 12. One or more of the modules depicted in the previous figures can be at least partially implemented on one or more distinct computer systems 1200.

Computer system 1200 includes one or more processors, such as processor 1204.

Processor 1204 can be a special purpose or a general purpose digital signal processor. Processor 1204 is connected to a communication infrastructure 1202 (for example, a bus or network). Various software implementations are described in terms of this exemplary computer system. After reading this description, it will become apparent to a person skilled in the relevant art(s) how to implement the disclosure using other computer systems and/or computer architectures.

Computer system 1200 also includes a main memory 1206, preferably random access memory (RAM), and may also include a secondary memory 1208. Secondary memory 1208 may include, for example, a hard disk drive 1210 and/or a removable storage drive 1212, representing a floppy disk drive, a magnetic tape drive, an optical disk drive, or the like. Removable storage drive 1212 reads from and/or writes to a removable storage unit 1216 in a well-known manner. Removable storage unit 1216 represents a floppy disk, magnetic tape, optical disk, or the like, which is read by and written to by removable storage drive 1212. As will be appreciated by persons skilled in the relevant art(s), removable storage unit 1216 includes a computer usable storage medium having stored therein computer software and/or data.

In alternative implementations, secondary memory 1208 may include other similar means for allowing computer programs or other instructions to be loaded into computer system 1200. Such means may include, for example, a removable storage unit 1218 and an interface 1214. Examples of such means may include a program cartridge and cartridge interface (such as that found in video game devices), a removable memory chip (such as an EPROM, or PROM) and associated socket, a thumb drive and USB port, and other removable storage units 1218 and interfaces 1214 which allow software and data to be transferred from removable storage unit 1218 to computer system 1200.

Computer system 1200 may also include a communications interface 1220. Communications interface 1220 allows software and data to be transferred between computer system 1200 and external devices. Examples of communications interface 1220 may include a modem, a network interface (such as an Ethernet card), a communications port, a PCMCIA slot and card, etc. Software and data transferred via communications interface 1220 are in the form of signals which may be electronic, electromagnetic, optical, or other signals capable of being received by communications interface 1220. These signals are provided to communications interface 1220 via a communications path 1222. Communications path 1222 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 1216 and 1218 or a hard disk installed in hard disk drive 1210. These computer program products are means for providing software to computer system 1200.

Computer programs (also called computer control logic) are stored in main memory 1206 and/or secondary memory 1208. Computer programs may also be received via communications interface 1220. Such computer programs, when executed, enable the computer system 1200 to implement the present disclosure as discussed herein. In particular, the computer programs, when executed, enable processor 1204 to implement the processes of the present disclosure, such as any of the methods described herein. Accordingly, such computer programs represent controllers of the computer system 1200. Where the disclosure is implemented using software, the software may be stored in a computer program product and loaded into computer system 1200 using removable storage drive 1212, interface 1214, or communications interface 1220.

In another embodiment, features of the disclosure are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

CONCLUSION

It is to be appreciated that the Detailed Description section, and not the Abstract section, is intended to be used to interpret the claims. The Abstract section may set forth one or more, but not all exemplary embodiments, and thus, is not intended to limit the disclosure and the appended claims in any way.

The disclosure has been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

It will be apparent to those skilled in the relevant art(s) that various changes in form and detail can be made therein without departing from the spirit and scope of the disclosure. Thus, the disclosure should not be limited by any of the above-described exemplary embodiments, but should be defined only in accordance with the following claims and their equivalents.

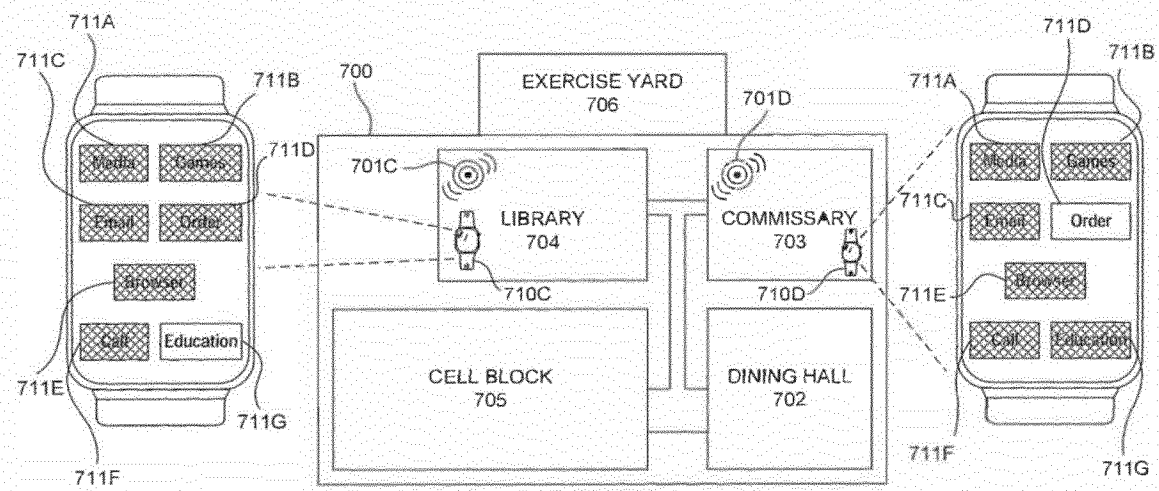

What is claimed is:

1. A method performed within a controlled environment, comprising:
   determining a location of a wearable device within the controlled environment and a proximity of the wearable device with at least one other wearable device;
   receiving, by the wearable device, an inmate profile of an inmate that includes information regarding a dynamic user interface of the wearable device;
   receiving, by the wearable device, an administrative rule that specifies a first restriction regarding an authorized function of the wearable device and a second restriction regarding a second authorized function, wherein the first restriction is a global restriction that applies to all inmates in the controlled environment and the second restriction is an inmate-specific restriction that is specific to the inmate;
verifying that the administrative rule is received from an authorized source associated with the controlled environment; performing the authorized function based at least on the inmate profile and the first restriction, wherein the authorized function includes customizing a setting of the dynamic user interface of the wearable device based on the inmate profile and the administrative rule; receiving location information from a first beacon configured to be located within a first location within the controlled environment, wherein the location information corresponds to the location of the wearable device;
displaying the dynamic user interface based at least in part on the customized setting and based on the location of the wearable device, wherein the displaying further comprises:
 preventing, on the dynamic user interface, access to a first application responsive to receiving the location information from the first beacon; and
 allowing, on the dynamic user interface, access to a second application responsive to the receiving the location information from the first beacon;
receiving second location information from a second beacon configured to be located within a second location with the controlled environment;
updating the dynamic user interface responsive to receiving the second location information from the second beacon;
performing the second authorized function based at least on the inmate profile and the second restriction, wherein the second authorized function includes a locking timer associated with a predetermined time period that the wearable device is attached to the inmate and wherein the second authorized function further includes activating a surveillance mode of the wearable device based on the proximity of the wearable device with the at least one other wearable device;
determining whether to unlock the wearable device based on the locking timer and the location of the wearable device within the controlled environment, wherein the wearable device is configured to be physically removable when unlocked.

2. The method of claim 1, wherein the authorized function comprises activating at least one component of the wearable device.

3. The method of claim 1, wherein the dynamic user interface includes a graphical keyboard, wherein the customizing the setting of the dynamic user interface comprises adjusting at least one of an arrangement of alphanumeric letters of the virtual graphical keyboard or a display setting of the graphical keyboard.

4. The method of claim 1, wherein the dynamic user interface includes displaying of applications specified by the inmate profile.

5. The method of claim 4, wherein the first restriction comprises a list of restricted applications, wherein the customizing the setting of the interface comprises restricting access to certain applications of the applications specified by the inmate profile based on the list of restricted applications.

6. The method of claim 4, wherein the displaying of applications is based at least in part on the location of the wearable device.

7. The method of claim 1, wherein the surveillance mode includes a biometric surveillance mode and the method further comprises:
 monitoring, by the wearable device, biometric information that includes at least one of heart rate information, oxygen information, and temperature information.

8. The method of claim 1, wherein the surveillance mode includes an environmental surveillance mode and the method further comprises:
 monitoring, by the wearable device, environmental information that includes at least one of audio information and video information regarding the controlled environment.

9. A wearable device, comprising:
a position module configured to provide position information of the wearable device, wherein the position information includes a location of the wearable device within a controlled environment and a proximity of the wearable device with at least one other wearable device;
a surveillance module configured to activate a surveillance mode of the wearable device based on the proximity of the wearable device with the at least one other wearable device;
a user interface module configured to customize a dynamic user interface of the wearable device based at least in part on an inmate profile and an administrative rule; and
a processor configured to:
 receive the inmate profile, wherein the inmate profile includes information regarding the user interface of the wearable device;
 receive the administrative rule, wherein the administrative rule specifies a first restriction regarding an authorized function of the wearable device and a second restriction regarding a second authorized function, wherein the first restriction is a global restriction that applies to all inmates in the controlled environment and the second restriction is an inmate-specific restriction that is specific to an inmate;
 instruct the user interface module to perform the authorized function, wherein the authorized function comprises customizing a setting of the dynamic user interface;
 receive location information from a first beacon configured to be located within a first location within the controlled environment, wherein the location information from the first beacon corresponds with the location of the wearable device;
 display the dynamic user interface based at least in part on the customized setting and based on the location of the wearable device, wherein to display the dynamic user interface, the processor is configured to:
  prevent, on the dynamic user interface, access to a first application responsive to receiving the location information from the first beacon; and
  allow, on the dynamic user interface, access to a second application responsive to receiving the location information from the first beacon;
 receive second location information from a second beacon configured to be located within a second location with the controlled environment;
 update the dynamic user interface responsive to receiving the second location information from the second beacon;

instruct the user interface module to perform the second authorized function; and determine whether to unlock the wearable device based on a locking timer associated with a predetermined time period that the wearable device is attached to the inmate and the location of the wearable device within the controlled environment, wherein the wearable device is configured to be physically removable when unlocked.

10. The wearable device of claim 9, further comprising: a locking module configured to lock the wearable device.

11. The wearable device of claim 9, further comprising: a gesture module configured to receive touch input and translate the touch input into a command that controls the dynamic user interface.

12. The wearable device of claim 9, wherein the dynamic user interface includes a graphical keyboard.

13. The wearable device of claim 12, wherein the user interface module is further configured to adjust at least one of an arrangement of alphanumeric letters of the graphical keyboard or a display setting of the graphical keyboard.

14. The wearable device of claim 9, wherein the second authorized function includes instructing the surveillance module to activate the surveillance mode of the wearable device, the surveillance information comprises biometric information, and wherein the activated surveillance mode is a biometric surveillance mode and the wearable device further comprises:

a biometric module configured to monitor the biometric information, wherein the biometric information includes at least one of heart rate information, oxygen information, and temperature information.

15. The wearable device of claim 9, wherein the second authorized function includes instructing the surveillance module to activate the surveillance mode of the wearable device, the surveillance information comprises environmental information, and wherein the activated surveillance mode is an environmental surveillance mode, wherein the surveillance module is further configured to monitor the environmental information, wherein the environmental information includes at least one of audio information and video information regarding the controlled environment.

16. A method, comprising:

providing, by a wearable device, a position location of the wearable device, wherein the position location is associated with a certain area within a controlled environment and a proximity of the wearable device with at least one other wearable device;

receiving, by the wearable device from an authorized source associated with the controlled environment, an administrative rule for controlling a surveillance mode of the wearable device based on the proximity of the wearable device with the at least one other wearable device and an interface instruction for controlling an operation of the wearable device;

performing an authorized function based at least on the interface instruction, wherein the authorized function comprises configuring a dynamic user interface of the wearable device;

receiving location information from a first beacon configured to be located within a first location within the controlled environment, wherein the location information from the first beacon corresponds with the position location of the wearable device;

displaying the dynamic user interface based on the position location of the wearable device, wherein the displaying further comprises:

preventing, on the dynamic user interface, access to a first application responsive to receiving the location information from the first beacon; and allowing, on the dynamic user interface, access to a second application responsive to receiving the location information from the first beacon;

receiving second location information from a second beacon configured to be located within a second location with the controlled environment;

updating the dynamic user interface responsive to receiving the second location information from the second beacon;

detecting a condition associated with a locking timer of the wearable device, wherein the condition is specified by the administrative rule;

performing a second authorized function based on the detected condition and the position location of the wearable device, wherein the second authorized function includes the locking timer associated with a predetermined time period that the wearable device is attached to an inmate; and determining whether to unlock the wearable device based on the locking timer and the position location of the wearable device, wherein the wearable device is configured to be physically removable when unlocked.

17. The method of claim 16, the interface instruction is received from a monitoring center associated with the controlled environment.

18. The method of claim 17, wherein configuring the dynamic user interface of the wearable device comprises adjusting a setting of the dynamic user interface, wherein the dynamic user interface includes a graphical keyboard.

19. The method of claim 17, further comprising:

receiving a deactivation signal from the monitoring center; and deactivating, based on the deactivation signal, the surveillance mode.

20. The method of claim 16, wherein the position location of the wearable device is a specific room in the controlled environment and the condition specified by the administrative rule specifies that the surveillance mode should be activated when the position location of the wearable device identifies the specific room.

* * * * *

UNITED STATES PATENT AND TRADEMARK OFFICE
CERTIFICATE OF CORRECTION

| | | |
|---|---|---|
| PATENT NO. | : 11,880,493 B2 | |
| APPLICATION NO. | : 15/469992 | |
| DATED | : January 23, 2024 | |
| INVENTOR(S) | : Hodge | |

It is certified that error appears in the above-identified patent and that said Letters Patent is hereby corrected as shown below:

On the Title Page

Item (72), in "Inventor", Line 1, delete "Aubry," and insert -- Aubrey, --, as shown on the attached page.

In the Drawings

On Sheet 8 of 19, delete figure "4E".

In the Specification

In Column 6, Line 28, delete "an" and insert -- a --, therefor.

In Column 15, Line 43, delete "an" and insert -- a --, therefor.

In Column 15, Line 49, after "letters" insert -- 407A, 407B, 407C, 407D, 407E, 407F, 407G, and 407H --, therefor.

In Column 20, Line 8, delete "an" and insert -- a --, therefor.

In the Claims

In Column 25, Claim 3, Line 55, before "graphical" delete "virtual".

Signed and Sealed this
Third Day of September, 2024

Katherine Kelly Vidal
*Director of the United States Patent and Trademark Office*

CERTIFICATE OF CORRECTION (continued)

(12) United States Patent
Hodge

(10) Patent No.: US 11,880,493 B2
(45) Date of Patent: Jan. 23, 2024

(54) WEARABLE DEVICES IN A CONTROLLED ENVIRONMENT

(71) Applicant: **GLOBAL TEL*LINK CORPORATION**, Reston, VA (US)

(72) Inventor: Stephen L. Hodge, Aubrey, TX (US)

(73) Assignee: **Global Tel*Link Corporation**, Reston, VA (US)

(*) Notice: Subject to any disclaimer, the term of this patent is extended or adjusted under 35 U.S.C. 154(b) by 1028 days.

(21) Appl. No.: 15/469,992

(22) Filed: Mar. 27, 2017

(65) Prior Publication Data
US 2018/0275859 A1    Sep. 27, 2018

(51) Int. Cl.
*G06F 21/00*    (2013.01)
*G06F 21/62*    (2013.01)
(Continued)

(52) U.S. Cl.
CPC ............ *G06F 21/629* (2013.01); *A61B 5/117* (2013.01); *A61B 5/1171* (2016.02); *A61B 5/681* (2013.01); *G06F 1/163* (2013.01); *G06F 1/1624* (2013.01); *G06F 1/1662* (2013.01); *G06F 1/1673* (2013.01); *G06F 3/0426* (2013.01);
(Continued)

(58) Field of Classification Search
CPC ..... A61B 5/117; A61B 5/681; A61B 5/14542; A61B 5/1171; A61B 5/024; A61B 5/01; G06F 1/163; G06F 2221/2111; G06F 3/04847; G06F 3/0481; G06F 3/0484; G06F 21/629; G06F 1/1673; G06F 21/34; G06F 1/1662; G06F 3/0426; G06F 1/1624; G06F 3/04886; G06F 3/0485; G06F 3/04883; G06F 3/0482; H04L 63/102; H04L 67/12; H04W 12/08
See application file for complete search history.

(56) References Cited

U.S. PATENT DOCUMENTS 4,495,386 A    1/1985  Brown et al.
5,255,306 A    10/1993 Melton et al.
(Continued)

FOREIGN PATENT DOCUMENTS

WO    WO-2016125063 A1 *  8/2016  ............ G04G 17/02

OTHER PUBLICATIONS

"Criminal Calls: A Review of the Bureau of Prisons' Management of Inmate Telephone Privileges," U.S. Department of Justice, Office of the Inspector General, Aug. 1999, 166 pages.
(Continued)

*Primary Examiner* — Cesar B Paula
*Assistant Examiner* — David Faber
(74) *Attorney, Agent, or Firm* — Sterne, Kessler, Goldstein & Fox P.L.L.C.

(57) ABSTRACT

A wearable device and method for operating the wearable device in a wearable device communication system in a controlled environment is disclosed. The wearable device includes at least one module configured to customize an inmate interface on the wearable device based at least in part of an inmate profile and an administrative rule. In some embodiments, the inmate interface is a keyboard. The wearable device also includes additional modules that enable the wearable device to monitor information regarding at least one of the inmate of the wearable device and the physical environment in which the wearable device is located.

20 Claims, 18 Drawing Sheets